US012673010B2

(12) United States Patent
Sakamoto et al.

(10) Patent No.: US 12,673,010 B2
(45) Date of Patent: Jul. 7, 2026

(54) DENTAL CERAMIC COLORING LIQUID HAVING MASKING PROPERTY

(71) Applicant: Kuraray Noritake Dental Inc., Kurashiki (JP)

(72) Inventors: Hiroyuki Sakamoto, Aichi (JP); Nobusuke Kashiki, Aichi (JP); Atsushi Matsuura, Aichi (JP)

(73) Assignee: KURARAY NORITAKE DENTAL INC., Kurashiki (JP)

(*) Notice: Subject to any disclaimer, the term of this patent is extended or adjusted under 35 U.S.C. 154(b) by 141 days.

(21) Appl. No.: 18/037,644

(22) PCT Filed: Nov. 18, 2021

(86) PCT No.: PCT/JP2021/042508
§ 371 (c)(1),
(2) Date: May 18, 2023

(87) PCT Pub. No.: WO2022/107867
PCT Pub. Date: May 27, 2022

(65) Prior Publication Data

US 2023/0404862 A1 Dec. 21, 2023

(30) Foreign Application Priority Data

Nov. 19, 2020 (JP) ................................ 2020-192848
Nov. 19, 2020 (JP) ................................ 2020-192849

(51) Int. Cl.
*A61K 6/896* (2020.01)
*A61K 6/65* (2020.01)
*A61K 6/818* (2020.01)

(52) U.S. Cl.
CPC ................ *A61K 6/896* (2020.01); *A61K 6/65* (2020.01); *A61K 6/818* (2020.01)

(58) Field of Classification Search
CPC ...................................................... A61K 6/896
See application file for complete search history.

(56) References Cited

U.S. PATENT DOCUMENTS

| | | | | |
|---|---|---|---|---|
| 3,400,097 A | 9/1968 | Weinstein et al. | | |
| 4,778,832 A * | 10/1988 | Futami | A61K 6/90 | 106/35 |
| 2006/0167217 A1* | 7/2006 | Okada | C08G 75/08 | 106/498 |
| 2012/0064490 A1 | 3/2012 | Rothbrust et al. | | |
| 2015/0344702 A1* | 12/2015 | Kim | C22C 18/00 | 428/626 |
| 2017/0105818 A1 | 4/2017 | Jahns et al. | | |
| 2019/0254788 A1* | 8/2019 | Tanaka | C04B 41/85 | |
| 2019/0388196 A1 | 12/2019 | Kitamura et al. | | |
| 2021/0355042 A1 | 11/2021 | Yan et al. | | |

FOREIGN PATENT DOCUMENTS

| | | | |
|---|---|---|---|
| CN | 104918900 A | 9/2015 | |
| CN | 109608233 A | 4/2019 | |
| EP | 252603 A * | 1/1988 | C09J 4/00 |
| JP | H08-269402 A | 10/1996 | |
| JP | 2013071921 A | 4/2013 | |
| JP | 2019181179 A | 10/2019 | |
| WO | WO-2004058196 A1 * | 7/2004 | A61K 6/10 |
| WO | WO-2020155446 A1 | 8/2020 | |

OTHER PUBLICATIONS

Extended European Search Report issued Oct. 4, 2024, received on Oct. 15, 2024, in corresponding European Patent Application No. 21894739.8, 6 pages.
International Search Report and Written Opinion issued Jan. 11, 2022 in PCT/JP2021/042508 (with English translation), 10 pages.
Robert F. Fedors, "A Method for Estimating Both the Solubility Parameters and Molar Volumes of liquids", Polymer Engineering and Science, vol. 14, No. 2, Feb. 1974, pp. 147-154.
Sinichi Ueda et al., "Discussion of Solubility Parameters of Excipients, Study on Solubility Parameter of Paint Additives", Paint Research, No. 152, Oct. 2010, pp. 41-46 (with English translation).

* cited by examiner

*Primary Examiner* — Michael F Pepitone
(74) *Attorney, Agent, or Firm* — Element IP, PLC

(57) ABSTRACT

The present invention provides a dental ceramic coloring liquid with which a decrease in the mechanical strength of a dental ceramic after sintering can be reduced, and that can impart masking properties while having good preservation stability. The present invention relates to a dental ceramic coloring liquid comprising an organosilicon compound. The organosilicon compound is preferably hydrophilic. The organosilicon compound is preferably a silicone compound. The organosilicon compound is preferably an alkylsilane compound.

12 Claims, No Drawings

DENTAL CERAMIC COLORING LIQUID HAVING MASKING PROPERTY

CROSS-REFERENCE TO RELATED APPLICATIONS

This application is a national stage entry of international application no. PCT/JP2021/042508, filed on Nov. 18, 2021, and claims priority to Japanese application nos. JP 2020-192848 and JP 2020-192849, both filed on Nov. 19, 2020.

TECHNICAL FIELD

The present invention relates to a coloring liquid for dental ceramics. Specifically, the invention relates to a dental ceramic coloring liquid suited for use in the fabrication of dental prostheses machined with a dental CAD/CAM system, for example, such as inlays, onlays, veneers, crowns, bridges, abutment teeth, dental posts, dentures, denture bases, and implant parts (fixtures, abutments).

BACKGROUND ART

Traditionally, metal has been used for a range of dental products, including, for example, dental prostheses (such as veneer crowns, dental caps, crowns, and post crowns), orthodontic products, and products for dental implants. However, metals lack aesthetic quality because of the colors that are distinctively different from the color of natural teeth, and can cause allergic reaction when released from these products. These issues involving the use of metal have been addressed by dental products that use a ceramic material such as aluminum oxide (alumina) or zirconium oxide (zirconia) as an alternative material of metal. Particularly, zirconia excels in strength, and has relatively good aesthetics, and this, combined in particular with the currently declining price of zirconia, has created a high demand for this material.

In recent years, there has been increasing use of a CAD/CAM system that makes use of a computer for designing and a milling machine for machining to form the final shape of a dental prosthesis, or to fabricate a prosthesis for large implants. For aesthetic values, such a system typically uses zirconia as a material of a mill blank to be milled. Particularly, recent years have seen increased use of zirconia that satisfies aesthetic requirements by reproducing the color of natural teeth with increased transmittance. For shades that are difficult to reproduce, a ceramic that has been worked into a shape of a dental prosthesis is colored by coating dental porcelain over a ceramic surface to satisfy high aesthetic requirements.

However, a consequence of the improved zirconia transmittance seen over the last years is that, because of the high total transmittance of zirconia, it has become increasing likely that the color is considerably affected by the color of, for example, remaining teeth or dental prostheses underneath zirconia (hereinafter, also referred to as "underlying color"; e.g., a color resulting from discoloration of underlying remaining teeth, or the color of a metallic dental prosthesis such as an implant abutment or a metal core), aside from the color of zirconia. When a dental prosthesis made from zirconia is coated over such underlying surfaces, aesthetics are compromised as a result of the dental prosthesis appearing darker than the intended color. This has created a need for a dental material capable of masking the influence of the underlying color.

Dental ceramic coloring liquids having masking properties are generally used as a way of solving this issue, as proposed below.

Patent Literature 1 discloses opacifying zirconia by containing a phosphorus component.

Patent Literature 2 discloses using a nitrate as a masking agent.

Patent Literature 3 discloses an opacity imparting liquid containing a water-soluble aluminum compound and/or a water-soluble lanthanum compound.

CITATION LIST

Patent Literature

Patent Literature 1: US Patent Application Publication Number 2017/105818

Patent Literature 2: WO2020/155446

Patent Literature 3: JP 2019-181179 A

SUMMARY OF INVENTION

Technical Problem

However, presumably, the phosphoric acid, phosphate, and other such components disclosed in Patent Literature 1 produce a rough zirconia surface after sintering, and the strength of the zirconia sintered body was found to decrease. Patent Literature 1 is intended to give zirconia a white color having masking properties, and does not suggest imparting a color so as to reproduce the color of natural teeth. The nitrate used in Patent Literature 2 has a safety issue because it decomposes, and generates toxic gases or causes an explosion when heated at a ceramic firing temperature. Studies by the present inventors revealed that, in Patent Literature 3, the masking properties to metallic abutment teeth are insufficient, and allow the color of an abutment tooth to be seen through. Patent Literature 3 is intended to impart masking properties to zirconia, and does not suggest imparting a color so as to reproduce the color of natural teeth.

It is accordingly an object of the present invention to provide a dental ceramic coloring liquid with which a decrease in the mechanical strength of a dental ceramic after sintering can be reduced, and that can impart masking properties while having good preservation stability. Another object of the present invention is to provide a dental ceramic coloring liquid that, when containing a coloring component, can impart the desired shade to a dental ceramic while imparting masking properties.

Solution to Problem

The present inventors conducted intensive studies to find a solution to the foregoing issues, and found that a coloring liquid capable of imparting high masking properties can be obtained by containing an organosilicon compound. The present invention was completed after further studies.

Specifically, the present invention includes the following.

[1] A coloring liquid for coloring a dental ceramic, comprising an organosilicon compound.

[2] The coloring liquid according to [1], wherein the organosilicon compound is hydrophilic.

[3] The coloring liquid according to [1] or [2], wherein the organosilicon compound is a silicone compound.

[4] The coloring liquid according to [3], wherein the silicone compound is a functional group-modified silicone compound.

[5] The coloring liquid according to [3] or [4], wherein the silicone compound is a polyether-modified silicone compound and/or a polyol-modified silicone compound.

[6] The coloring liquid according to [5], wherein the polyether-modified silicone compound or the polyol-modified silicone compound is a compound represented by general formula (1),

[Chem. 1]

(1)

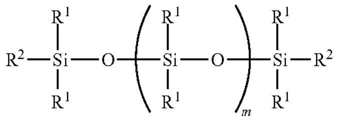

wherein R 1 may be the same or different, and each represent an optionally substituted linear or branched alkyl group, or an optionally substituted aryl group, m is an integer of 1 or more, and R 2 may be the same or different, and each represent a polyether group or a polyol group.

[7] The coloring liquid according to [6], wherein the silicone compound is a compound having a main chain with a dimethylpolysiloxane group in which R 1 are all methyl groups.

[8] The coloring liquid according to any one of [3] to [7], wherein the silicone compound is liquid at ordinary temperature.

[9] The coloring liquid according to any one of [3] to [8], wherein the content of the silicone compound is 0.1 to 60 mass %.

[10] The coloring liquid according to [1] or [2], wherein the organosilicon compound is an alkylsilane compound.

[11] The coloring liquid according to [10], wherein the alkylsilane compound is a compound represented by the following general formula (2),

[Chem. 2]

(2)

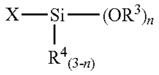

wherein $R^3$ represents an optionally substituted linear or branched alkyl group, $R^4$ represents an optionally substituted linear or branched alkyl group, an optionally substituted aryl group, or a halogen atom, n is an integer of 0 to 3, and X represents $—R^5—Y^1$, $—R^5—B^1\text{-}A^1$, $—R^5\text{-}A^1$, or $\text{-}A^1$, where $R^5$ is an optionally substituted linear or branched alkylene group or a cycloalkylene group, and the alkylene group or the cycloalkylene group may contain a $—CH_2—C_6H_4—$ ($C_6H_4$ represents a phenylene group), —S—, —NH—, $—NR^6—$, —C(O)—O—, or —O— group, where $R^6$ represents an optionally substituted linear or branched alkyl group, an optionally substituted cycloalkyl group, or an optionally substituted aryl group, $Y^1$ represents a hydroxyl group, an optionally substituted alkoxy group, an optionally substituted amino group, a mercapto group, an epoxy group, a halogen atom, or an optionally substituted amine salt, $B^1$ represents —C(O)—O—, —C(O)—S—, —C(O)—NH—, —NH—C(O)—NH—, —NH—C(O)—S—, or —NH—C(O)—O—, and $A^1$ represents $H_2C{=}CH—$, $H_2C{=}C(CH_3)—$, or $H_2C{=}CH—C_6H_4—$ ($C_6H_4$ represents a phenylene group).

[12] The coloring liquid according to [11], wherein, in compounds represented by the general formula (2), X represents $—R^5—Y^1$ or $—Y^1$, and $Y^1$ is a hydroxyl group, an optionally substituted amino group, an epoxy group, or an optionally substituted amine salt.

[13] The coloring liquid according to [12], wherein X represents $—R^5—Y^1$, $R^5$ is an optionally substituted linear or branched alkylene group, and the alkylene group may contain a $—CH_2—C_6H_4—$ ($C_6H_4$ represents a phenylene group), —S—, —NH—, $—NR^6—$, —C(O)—O—, or —O— group.

[14] The coloring liquid according to any one of to [13], wherein the alkylsilane compound is at least one compound selected from the group consisting of trimethylsilanol, 2-(3,4-epoxycyclohexyl)ethyltrimethoxysilane, 3-glycidoxypropylmethyldimethoxysilane, 3-glycidoxypropyltrimethoxysilane, 3-glycidoxypropylmethyldiethoxysilane, 3-glycidoxypropyltriethoxysilane, N-2-(aminoethyl)-3-am inopropylmethyldimethoxysilane, N-2-(aminoethyl)-3-aminopropyltrimethoxysilane, 3-phenylaminopropyltrimethoxysilane, 3-aminopropyltrimethoxysilane, and 3-am inopropyltriethoxysilane.

[15] The coloring liquid according to any one of to [14], wherein the content of the alkylsilane compound is 0.1 to 60 mass %.

[16] The coloring liquid according to any one of [1] to [15], which further comprises a coloring component.

[17] The coloring liquid according to [16], wherein the coloring component is an ion or a complex.

[18] The coloring liquid according to or [17], wherein the coloring component comprises at least one component selected from the group consisting of Al, K, Zr, Cr, Fe, Na, V, Y, Gd, La, Yb, Tm, Ni, Mn, Co, Nd, Pr, Cu, Tb, and Er.

[19] The coloring liquid according to any one of [1] to [18], which further comprises water and/or an organic solvent.

[20] The coloring liquid according to [19], wherein the organic solvent comprises at least one selected from the group consisting of an alcohol, a glycol, a triol, and a ketone.

[21] The coloring liquid according to any one of [1] to [20], wherein the dental ceramic comprises zirconia as a main component.

[22] A dental ceramic supporting an organosilicon compound on a surface of the dental ceramic.

[23] The dental ceramic according to [22], wherein the organosilicon compound is hydrophilic.

[24] The dental ceramic according to or [23], wherein the organosilicon compound is a silicone compound.

[25] The dental ceramic according to [24], wherein the silicone compound is a polyether-modified silicone compound and/or a polyol-modified silicone compound.

[26] The dental ceramic according to or [23], wherein the organosilicon compound is an alkylsilane compound.

[27] The dental ceramic according to [26], wherein the alkylsilane compound is a compound represented by the following general formula (2),

[Chem. 3]

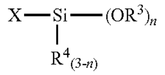

(2)

wherein $R^3$ represents an optionally substituted linear or branched alkyl group, $R^4$ represents an optionally substituted linear or branched alkyl group, an optionally substituted aryl group, or a halogen atom, n is an integer of 0 to 3, and X represents $—R^5—Y^1$, $—R^5—B^1\text{-}A^1$, $—R^5\text{-}A^1$, or $\text{-}A^1$, where $R^5$ is an optionally substituted linear or branched alkylene group or a cycloalkylene group, and the alkylene group or the cycloalkylene group may contain a $—CH_2—C_6H_4—$ ($C_6H_4$ represents a phenylene group), —S—, —NH—, $—NR^6—$, —C(O)—O—, or —O— group, where $R^6$ represents an optionally substituted linear or branched alkyl group, an optionally substituted cycloalkyl group, or an optionally substituted aryl group, $Y^1$ represents a hydroxyl group, an optionally substituted alkoxy group, an optionally substituted amino group, a mercapto group, an epoxy group, a halogen atom, or an optionally substituted amine salt, $B^1$ represents —C(O)—O—, —C(O)—S—, —C(O)—NH—, —NH—C(O)—NH—, —NH—C(O)—S—, or —NH—C(O)—O—, and Al represents $H_2C{=}CH—$, $H_2C{=}C(CH_3)—$, or $H_2C{=}CH—C_6H_4—$ ($C_6H_4$ represents a phenylene group).

[28] The dental ceramic according to [27], wherein, in compounds represented by the general formula (2), X represents $—R^5—Y^1$ or $—Y^1$, and $Y^1$ is a hydroxyl group, an optionally substituted amino group, an epoxy group, or an optionally substituted amine salt.

[29] The dental ceramic according to any one of to [28], which additionally supports a coloring component.

[30] The dental ceramic according to [29], wherein the coloring component is an ion or a complex.

[31] The dental ceramic according to or [30], wherein the coloring component comprises at least one component selected from the group consisting of Al, K, Zr, Cr, Fe, Na, V, Y, Gd, La, Yb, Tm, Ni, Mn, Co, Nd, Pr, Cu, Tb, and Er.

Advantageous Effects of Invention

A dental ceramic coloring liquid of the present invention can reduce a decrease in the mechanical strength of a dental ceramic after sintering, and can impart masking properties while having good preservation stability. A dental ceramic coloring liquid of the present invention, when containing a coloring component, can impart the desired shade to a dental ceramic while imparting masking properties. A dental ceramic coloring liquid of the present invention is easier to use than dental porcelain because a dental ceramic coloring liquid of the present invention, unlike dental porcelain, is not required to have properties needed by dental porcelain, such as a coefficient of thermal expansion suited for a ceramic frame to enable good bonding to a ceramic frame, and durability in the oral cavity.

DESCRIPTION OF EMBODIMENTS

The present invention is a coloring liquid for coloring a dental ceramic, and comprises an organosilicon compound.

Organosilicon Compound

First, an organosilicon compound is described that is contained in a coloring liquid of the present invention as a masking component that imparts masking properties to a dental ceramic. By masking the influence of an underlying color such as discoloration of underlying remaining teeth, or the color of a metallic dental prosthesis such as an implant abutment or a metal core, the organosilicon compound of the present invention can impart a white tint to the shade of a dental ceramic to give color. The organosilicon compound used in the present invention has good preservation stability. With the organosilicon compound, it is also possible to reduce a decrease in the mechanical strength of a sintered body obtained after sintering when a dental ceramic is sintered. In the present invention, the term "coloring" is used not only when giving a color other than white, but when simply giving a white tint by masking the influence of the underlying color. As used herein, "coloring liquid" describes a liquid agent used for coloring. In contrast, "coloring component" (described later) means an optional component for giving a color other than white to a dental ceramic (for example, imparting a predetermined chroma to a dental ceramic).

The masking properties of a dental ceramic after firing can improve by applying a dental ceramic coloring liquid containing an organosilicon compound. Though the reason for this remains unclear, the present inventors have proposed the following explanation. Specifically, at least a part of the organosilicon compound applied to a dental ceramic turns into silicon dioxide ($SiO_2$) while being fired, and a part of the silicon dioxide combines with zirconia ($ZrO_2$) to partially generate zircon ($ZrSiO_4$). Presumably, the partial presence of a crystalline phase different from the sintered ceramic causes scattering of incident light, and creates opacity.

With a coloring liquid of the present invention, the masking properties needed for dental use can be imparted to a dental ceramic. By decreasing transparency in this fashion, the surface of the target object can be opacified to mask the influence of the underlying color. In view of maintaining the lightness that needs to be reproduced in the oral cavity for a dental ceramic after sintering in dental use, the transparency ($\Delta L^*$) is preferably 11 or less, more preferably 10 or less, even more preferably 9 or less, where $\Delta L^*$ ($\Delta L^* = (Lw^*) - (Lb^*)$) is the difference between lightness ($Lw^*$) and lightness ($Lb^*$) measured against a white background and a black background, respectively, in a chromaticity measurement of ($L^*,a^*,b^*$) of a dental ceramic after coloring and sintering according to L*a*b*color system (JIS Z 8781-4: 2013 Color Measurements—Part 4: CIE 1976 L*a*b* color space). The transparency ($\Delta L^*$) can be evaluated using, for example, the method described in the EXAMPLES section below.

A coloring liquid of the present invention, when containing a coloring component (described later), can impart the shade needed for dental use to a dental ceramic, while imparting masking properties to a dental ceramic. A dental ceramic after coloring and sintering has an a* value of preferably −5 to 5, more preferably −4 to 4, even more preferably −3 to 3 in ($L^*,a^*,b^*$) of L*a*b*color system. The b* value is preferably 0.5 to 25, more preferably 1 to 22, even more preferably 2 to 20. Preferably, the chroma calculated from a* and b* ($C^*=((a^*)^2+(b^*)^2)^{1/2}$) is 0.5 to 25, more preferably 1 to 22, even more preferably 2 to 20. L* is preferably 70 to 97, more preferably 75 to 96, even more preferably 80 to 95. The a*, b*, and L* values can be measured using, for example, the method described in the EXAMPLES section below.

In view of penetrability into a dental ceramic and solubility in water or the like, the organosilicon compound of the present invention is preferably a hydrophilic compound. In the present invention, "hydrophilic" means that the solubility in pH 7 water at 25° C. is 0.5 mass % or more. Preferably, the solubility is 5 mass % or more. The organosilicon compound may be, for example, a silicone compound or an alkylsilane compound. The organosilicon compound may be used alone, or two or more thereof may be used in combination.

The content of the organosilicon compound contained in the coloring liquid is preferably 0.1 to 60 mass %, more preferably 0.3 to 58 mass %, even more preferably 0.5 to 55 mass % relative to the total amount of the coloring liquid. With 0.1 mass % or more of organosilicon compound, it is possible to provide masking properties against an underlying color such as discoloration of remaining teeth. With 60 mass % or less of organosilicon compound, superior penetration into a dental ceramic can be obtained.

In view of high preservation stability and high masking properties to a dental ceramic after firing, it is preferable in a certain embodiment that the organosilicon compound used in a coloring liquid of the present invention be a silicone compound. Below is a description of a silicone compound. In the present invention, the silicone compound is preferably a polymeric compound comprising siloxane bonds as the backbone.

Silicone Compound

The silicone compound of the present invention is a polymer having a framework formed by siloxane bonds composed of silicon and oxygen, and in which an organic group, mainly alkyl, aryl, or other such group, is attached to the silicon. Preferably, the silicone compound is a hydrophilic silicone compound in the present invention, as noted above. It is accordingly preferable in view of penetrability into a dental ceramic and solubility in water or the like that the silicone compound be a functional group-modified silicone compound having an organic functional group that imparts hydrophilicity. In view of even superior preservation stability, the silicone compound is more preferably a polyether-modified silicone compound and/or a polyol-modified silicone compound, even more preferably a polyether-modified silicone compound and/or a polyol-modified silicone compound represented by general formula (1). The functional group of the organic functional group-modified silicone compound is not particularly limited, and can be selected from any functional groups, provided that it provides excellent penetrability into dental ceramics, and high solubility in water or the like.

[Chem. 4]

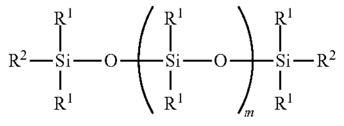

(1)

In the formula, $R^1$ may be the same or different, and each represent an optionally substituted linear or branched alkyl group, or an optionally substituted aryl group, m is an integer of 1 or more, and $R^2$ may be the same or different, and each represent a polyether group or a polyol group.

The optionally substituted linear or branched alkyl group represented by $R^1$ is not particularly limited, and is preferably an alkyl group having 1 to 6 carbon atoms, more preferably an alkyl group having 1 to 4 carbon atoms. In view of penetrability into a dental ceramic and solubility in water or the like, an alkyl group having 1 to 3 carbon atoms is even more preferred. Examples of the alkyl groups of $R^1$ and $R^2$ include methyl, ethyl, n-propyl, isopropyl, n-butyl, isobutyl, sec-butyl, 2-methylpropyl, tert-butyl, n-pentyl, isopentyl, sec-pentyl, neopentyl, and n-hexyl. The optionally substituted aryl group represented by $R^1$ may be, for example, phenyl or naphthyl. Examples of the substituents include an alkyl group having 1 to 6 carbon atoms (preferably, 1 to 3 carbon atoms), an alkoxy group having 1 to 6 carbon atoms (preferably, 1 to 3 carbon atoms), halogen atoms (fluorine atom, chlorine atom, bromine atom, iodine atom), and a hydroxyl group. The number of substituents is not particularly limited, and may be 1 to 6, 1 to 4, or 0, provided that the silicone compound has penetrability into a dental ceramic and solubility in water or the like.

In view of penetrability into a dental ceramic and solubility in water or the like, $R^1$ is preferably an optionally substituted linear or branched alkyl group.

The polyether group represented by $R^2$ is not particularly limited, as long as it is a group containing a polyalkylene glycol structure, and may be, for example, a group such as polyethylene glycol, polypropylene glycol, or a polyethylene glycol-polypropylene glycol copolymer. The polyol group is not particularly limited, as long as it is a group having two or more hydroxyl groups (for example, an aliphatic group), and may be, for example, a group such as polyether polyol or polyester polyol.

It is preferable in the silicone compound that the main chain having siloxane bonds (hereinafter, also referred to as "siloxane main chain") be a dimethylpolysiloxane group in which $R^1$ are all methyl groups. When the siloxane main chain is a dimethylpolysiloxane group, the silicone compound has a spiral framework structure, and presumably improves the penetration into a dental ceramic.

In view of penetrability into a dental ceramic and solubility in water or the like, the silicone compound is preferably one that is liquid at ordinary temperature (20 to 35° C.).

When the silicone compound is rubbery or solid at ordinary temperature, it may not be possible to provide sufficient masking properties as a result of insufficient penetration into a dental ceramic due to the increased molecular weight or a decrease of hydrophilicity. In view of penetrability into a dental ceramic and solubility in water or the like, it is preferable in the silicone compound that the number of siloxane bonds in the siloxane main chain be 2,000 or less (m=1,998 or less in the case of compounds represented by general formula (1)). When the number of siloxane bonds is more than 2,000, it may not be possible to provide sufficient masking properties as a result of insufficient penetration into a dental ceramic due to the increased molecular weight or a decrease of hydrophilicity.

In view of penetrability into a dental ceramic and solubility in water or the like, the silicone compound has a solubility parameter (hereinafter, "SP value") of preferably 8.2 $(cal/cm^3)^{1/2}$ or more, more preferably 8.4 $(cal/cm^3)^{1/2}$ or more, even more preferably 8.6 $(cal/cm^3)^{1/2}$ or more. With an SP value of less than 8.2 $(cal/cm^3)^{1/2}$, it may not be possible to provide sufficient masking properties as a result of insufficient penetration into a dental ceramic, and problems such as sedimentation or separation may occur because of poor dissolution in water solvent.

The SP value is represented by the square root of intermolecular attraction force, that is, cohesive energy density (CED). CED describes the amount of energy needed to evaporate 1 mL of a liquid.

The SP value can be calculated by the Fedors method, using the following formula (A).

$$\text{SP value}=(\text{CED value})^{1/2}=(E/V)^{1/2} \qquad \text{Formula (A)}$$

In the formula (A), E represents the cohesive energy (cal/mol), and V represents the molar molecular volume ($cm^3$/mol). Of the various methods available for the calculation of SP value, the present invention employs the commonly used Fedors method.

As a reference, the method of calculation, and various data for cohesive energy E and molar molecular volume V can be found in *Research on Coatings*, Vol. 152, Published October, 2010, pp. 41 to 46 (Study on Solubility Parameter of Paint Additives by Shinichi Ueda, Tomoo Yamada, and Masami Sugishima) (e.g., Econ and molar molecular volumes in Table 2, page 42; and Fedors values in Table 3), and in R. F. Fedors, Polymer Engineering & Science. Feb., Vol. 14, No. 2, 147-154 (1974).

The silicone compound may be a commercially available product. Examples of such commercially available products include polyether-modified silicone KP-120, KP-106, KP-110, KP-101, KP-125, and KP-112 (all manufactured by Shin-Etsu Chemical Co., Ltd. under these trade names), and polyol-modified silicone KP-104 and KP-105 (both manufactured by Shin-Etsu Chemical Co., Ltd. under these trade names).

The content of the silicone compound contained in the coloring liquid is preferably 0.1 to 60 mass %, more preferably 0.3 to 58 mass %, even more preferably 0.5 to 55 mass % relative to the total amount of the coloring liquid. With 0.1 mass % or more of silicone compound, it is possible to provide masking properties against an underlying color such as discoloration of remaining teeth. With 60 mass % or less of silicone compound, superior penetration into a dental ceramic can be obtained.

In view of high preservation stability and high masking properties to a dental ceramic after firing, it is preferable in another certain embodiment that the organosilicon compound used for a coloring liquid of the present invention be an alkylsilane compound. Below is a description of an alkylsilane compound.

Alkylsilane Compound

The following first describes the alkylsilane compound contained in a dental ceramic coloring liquid of the present invention. By masking the influence of an underlying color such as discoloration of underlying remaining teeth, or the color of a metallic dental prosthesis such as an implant abutment or a metal core, the alkylsilane compound of the present invention can impart a white tint to the shade of a dental ceramic to give color. The alkylsilane compound used in the present invention has good preservation stability. With the alkylsilane compound, it is also possible to reduce a decrease in the mechanical strength of a sintered body obtained after sintering when a dental ceramic is sintered. In the present invention, an alkylsilane compound is a silane compound having an alkyl group. The alkyl group may be optionally substituted.

In view of penetrability into a dental ceramic and solubility in water or the like, the alkylsilane compound of the present invention is preferably hydrophilic.

In view of superior preservation stability and superior masking properties, and the ability to more greatly reduce a decrease in the mechanical strength of a sintered body, the alkylsilane compound of the present invention is preferably a compound with a molecular structure represented by the following general formula (2).

[Chem. 5]

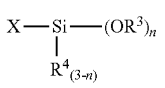

(2)

In the formula, $R^3$ represents an optionally substituted linear or branched alkyl group, $R^4$ represents an optionally substituted linear or branched alkyl group, an optionally substituted aryl group, or a halogen atom, n is an integer of 0 to 3, and X represents $—R^5—Y^1$, $—R^5—B^1\text{-}A^1$, $—R^5\text{-}A^1$, or $\text{-}A^1$, where $R^5$ is an optionally substituted linear or branched alkylene group or a cycloalkylene group, and the alkylene group or the cycloalkylene group may contain a $—CH_2—C_6H_4—$ ($C_6H_4$ represents a phenylene group), —S—, —NH—, $—NR^6—$, —C(O)—O—, or —O— group, where $R^6$ represents an optionally substituted linear or branched alkyl group, an optionally substituted cycloalkyl group, or an optionally substituted aryl group, $Y^1$ represents a hydroxyl group, an optionally substituted alkoxy group, an optionally substituted amino group, a mercapto group, an epoxy group, a halogen atom, or an optionally substituted amine salt, $B^1$ represents —C(O)—O—, —C(O)—S—, —C(O)—NH—, —NH—C(O)—NH—, —NH—C(O)—S—, or —NH—C(O)—O—, and Al represents $H_2C{=}CH—$ (vinyl group), $H_2C{=}C(CH_3)$-(1-methylethenyl group), or $H_2C{=}CH—C_6H_4—$ ($C_6H_4$ represents a phenylene group).

The optionally substituted linear or branched alkyl groups represented by $R^3$ and $R^4$ are not particularly limited. Preferred are alkyl groups having 1 to 6 carbon atoms, more preferably alkyl groups having 1 to 4 carbon atoms, even more preferably alkyl groups having 1 to 3 carbon atoms. Examples of the alkyl groups of $R^3$ and $R^4$ include methyl, ethyl, n-propyl, isopropyl, n-butyl, isobutyl, sec-butyl, 2-methylpropyl, tert-butyl, n-pentyl, isopentyl, sec-pentyl, neopentyl, and n-hexyl. Examples of the halogen atom include a fluorine atom, a chlorine atom, a bromine atom, and an iodine atom. Examples of the optionally substituted aryl group represented by $R^4$ include phenyl and naphthyl. Preferred is a phenyl group. Examples of the substituents of the alkyl groups of $R^3$ and $R^4$, and the substituents of the aryl group of $R^4$ include an alkyl group having 1 to 6 carbon atoms (preferably, 1 to 3 carbon atoms), an alkoxy group having 1 to 6 carbon atoms (preferably, 1 to 3 carbon atoms), a phenyl group, a halogen atom (fluorine atom, chlorine atom, bromine atom, iodine atom), and a hydroxyl group. The number of substituents is not particularly limited, and may be 1 to 6, 1 to 4, or 0, as long as the alkylsilane compound has penetrability into a dental ceramic and solubility in water or the like. In certain embodiments, $R^3$ represents an unsubstituted linear or branched alkyl group, and $R^4$ represents an unsubstituted linear or branched alkyl group, an unsubstituted phenyl group, or a halogen atom in compounds represented by general formula (2).

The optionally substituted linear or branched alkylene group represented by $R^5$ is not particularly limited, and is preferably an alkylene group having 1 to 8 carbon atoms, more preferably an alkylene group having 1 to 6 carbon atoms, even more preferably an alkylene group having 1 to 4 carbon atoms, particularly preferably an alkylene group having 1 to 3 carbon atoms. Examples of the alkylene group include a methylene group, an ethylene group, a n-propylene group, an isopropylene group, a n-butylene group, a n-pentylene group, and a n-hexylene group. The linear or branched cycloalkylene group represented by $R^5$ is not particularly limited, and is preferably a cycloalkylene group having 3 to 10 carbon atoms, more preferably a cycloalkylene group having 4 to 8 carbon atoms, even more preferably a cycloalkylene group having 4 to 7 carbon atoms. Examples of the cycloalkylene groups include a cyclopropylene group, a cyclobutylene group, a cyclopentylene group, and a cyclohexylene group (for example, 1,2-cyclohexylene group, 1,3-cyclohexylene group, 1,4-cyclohexylene group). The type and number of substituents in the alkylene group and cycloalkylene group represented by $R^5$ are the same as that of the substituents of the alkyl groups of $R^3$ and $R^4$.

The alkylene group or cycloalkylene group represented by $R^5$ may contain a —$CH_2$—$C_6H_4$— ($C_6H_4$ represents a phenylene group), —S—, —NH—, —$NR^6$—, —C(O)—O—, or —O— group as a binding group. In other words, the alkylene group or cycloalkylene group may be interrupted with a —$CH_2$—$C_6H_4$— ($C_6H_4$ represents a phenylene group), —S—, —NH—, —$NR^6$—, —C(O)—O—, or —O— group. Specifically, $R^5$ may be, for example, —$C_2H_4$—NH—$C_3H_6$—, —$CH_2$—NH—$C_2H_4$—NH—$C_3H_6$—, or —$CH_2$—O—$C_3H_6$—. The alkyl group and aryl group of $R^6$ are the same as in $R^4$. Examples of the cycloalkyl group of $R^6$ include a cyclopropyl group, a cyclobutyl group, a cyclopentyl group, and a cyclohexyl group. The type and number of substituents in the alkyl group, cycloalkyl group, and aryl group of $R^6$ are the same as that of the substituents of the alkyl groups of $R^3$ and $R^4$.

Preferably, $B^1$ is —C(O)—O—, —C(O)—NH—, —NH—C(O)—NH—, or —NH—C(O)—O—. Preferably, Al is $H_2C$═CH— or $H_2C$═C($CH_3$)—. Preferably, $Y^1$ is a hydroxyl group, an optionally substituted amino group, an epoxy group, or an optionally substituted amine salt.

More preferred among these are compounds in which X represents —$R^5$—$Y^1$ or —$Y^1$. In view of penetrability into a dental ceramic and solubility in water or the like, even more preferred are compounds in which X represents —$R^5$—$Y^1$ or —$Y^1$, and $Y^1$ is a hydroxyl group, an optionally substituted amino group, an epoxy group, or an optionally substituted amine salt. A certain preferred embodiment is, for example, a dental ceramic coloring liquid in which, in compounds represented by general formula (2), X represents —$R^5$—$Y^1$, $R^5$ is a linear or branched alkylene group, and the alkylene group may contain a —$CH_2$—$C_6H_4$— ($C_6H_4$ represents a phenylene group), —S—, —NH—, —$NR^6$—, —C(O)—O—, or —O— group. The type and number of substituents in the alkoxy group, amino group, and amine salt of $Y^1$ are the same as that of the substituents of the alkyl groups of $R^3$ and $R^4$.

Examples of specific compounds include:

amino group-containing alkylsilane compounds such as N-2-(aminoethyl)-3-am inopropylmethyldimethoxysilane,
N-2-(aminoethyl)-3-aminopropyltrimethoxysilane,
N-2-(aminoethyl)-3-aminopropyltriethoxysilane,
3-[2-(2-aminoethylamino)ethylamino]propyltrimethoxysilane,
3-aminopropyltrimethoxysilane, 3-am inopropyltriethoxysilane, and
3-phenylaminopropyltrimethoxysilane;

epoxy group-containing alkylsilane compounds such as 3-triethoxysilyl-N-(1,3-dimethyl-butylidene)propylamine,
2-(3,4-epoxycyclohexyl)ethyltrimethoxysilane, 3-glycidoxypropylmethyldimethoxysilane,
3-glycidoxypropyltrimethoxysilane, 3-glycidoxypropylmethyldiethoxysilane,
3-glycidoxypropyltriethoxysilane, and 2-(3,4-epoxycyclohexyl)ethyltrimethoxysilane;

vinyl group-containing alkylsilane compounds such as a hydrochloride of N-(vinylbenzyl)-2-aminoethyl-3-aminopropyltrimethoxysilane; and hydroxyl group-containing alkylsilane compounds such as trimethylsilanol, trimethylsilylmethanol, and trimethylsilylethanol.

Preferred is at least one selected from the group consisting of trimethylsilanol, 2-(3,4-epoxycyclohexyl)ethyltrimethoxysilane, 3-glycidoxypropylmethyldimethoxysilane, 3-glycidoxypropyltrimethoxysilane, 3-glycidoxypropylmethyldiethoxysilane, 3-glycidoxypropyltriethoxysilane, N-2-(aminoethyl)-3-aminopropylmethyldimethoxysilane, N-2-(aminoethyl)-3-aminopropyltrimethoxysilane, 3-phenylaminopropyltrimethoxysilane, 3-aminopropyltrimethoxysilane, and 3-am inopropyltriethoxysilane. More preferred is at least one selected from the group consisting of 3-glycidoxypropylmethyldimethoxysilane, 3-glycidoxypropyltrimethoxysilane, 3-glycidoxypropylmethyldiethoxysilane, 3-glycidoxypropyltriethoxysilane, N-2-(aminoethyl)-3-aminopropylmethyldimethoxysilane, N-2-(aminoethyl)-3-aminopropyltrimethoxysilane, 3-aminopropyltrimethoxysilane, and 3-am inopropyltriethoxysilane.

The content of the alkylsilane compound contained in a coloring liquid of the present invention is preferably 0.1 to 60 mass %, more preferably 0.3 to 58 mass %, even more preferably 0.5 to 55 mass % relative to the total amount of the coloring liquid. With 0.1 mass % or more of alkylsilane compound, it is possible to provide masking properties against an underlying color such as discoloration of remaining teeth. With mass % or less of alkylsilane compound, superior preservation stability can be obtained.

Another certain embodiment is, for example, a dental ceramic coloring liquid comprising an organosilicon compound (for example, a silicone compound, an alkylsilane compound), and a coloring component. Presumably, the coloring component can be contained because the organosilicon compound contained in the coloring liquid has good preservation stability, and does not react with the coloring component. This makes it possible to impart the desired shade to a dental ceramic while imparting masking properties. A coloring component in the present invention is a component that colors a ceramic sintered body when a ceramic pre-sintered body or unfired body is sintered after the application of the coloring liquid.

The coloring component is not particularly limited, and may be ions or complexes. Metal ions, in particular, are preferred. The coloring component may be used alone, or two or more thereof may be used in combination.

Ions and complexes of the coloring component used in the present invention are described below. Ions and complexes of the coloring component comprise one or more colorative cations. Here, "colorative" means having significant absorption in the human visible spectrum (for example, 380 to 790 nm wavelengths). In the present invention, a colorative cation develops a color after being fired. The ions and complexes of the present invention can dissolve colorative cations, and, by dissolving colorative cations, can coat a ceramic pre-sintered body or unfired body, and color a ceramic sintered body after firing.

The colorative cation is preferably an ion of at least one component (element) selected from the group consisting of Al, K, Zr, Cr, Fe, Na, V, Y, Gd, La, Yb, Tm, Ni, Mn, Co, Nd, Pr, Cu, Tb, and Er, more preferably an ion of at least one component selected from the group consisting of Al, K, Cr, Fe, Na, V, Ni, Mn, Co, and Er, even more preferably an ion of at least two components selected from the group consisting of Al, K, Cr, Fe, Na, V, Ni, Mn, Co, and Er. The ion solution may contain only one of these cations, or may contain two or more of these cations in combination.

The colorative cation may be added in the solvent (described later) in the forms of salts containing cations, such as above, and anions. Examples of the anions include $OAc^-$, $NO_3^-$, $NO_2^-$, $CO_3^{2-}$, $HCO_3^-$, $ONC^-$, $SCN^-$, $SO_4^{2-}$, $SO_3^{2-}$, glutarate, lactate, gluconate, propionate, butyrate, glucuronate, benzoate, phenolate, halide anions (fluorides, chlorides, bromides), and acetate. Ac means acetyl group.

A certain preferred embodiment of the present invention is, for example, a coloring liquid in which the coloring component comprises a V (vanadium) component to give a yellow tinged shade to a dental ceramic.

Ions or complexes of V may be added in the coloring liquid in the form of salts containing cations and anions of V, or in the form of complexes containing V and ligands. Examples of the anions or ligands include $OAc^-$, $NO_3^-$, $NO_2^-$, $CO_3^{2-}$, $HCO_3^-$, $ONC^-$, $SCN^-$, $SO_4^{2-}$, $SO_3^{2-}$, glutarate, lactate, gluconate, propionate, butyrate, glucuronate, benzoate, phenolate, halide anions (fluorides, chlorides, bromides), and acetate.

In view of preservation stability and ease of handling, the vanadium compound is preferably a vanadium compound with a valency of +IV and/or +V, more preferably an oxidovanadium compound.

Specific examples of compounds as V components include vanadium acetylacetonate, vanadyl acetylacetonate, vanadyl stearate, vanadium naphthenate, vanadium benzoylacetonate, vanadyl oxalate, bis(maltolato)oxovanadium (IV), oxobis(1-phenyl-1,3-butanedionate)vanadium, vanadium(V) oxytriisopropoxide, vanadium(V) trichloride oxide, vanadium(IV) dichloride oxide, vanadium(III) chloride hydrate (hexahydrate), vanadium(III) chloride anhydrous, vanadium disilicide, vanadium(III) oxide, vanadium(IV) oxide, vanadium(V) oxide, iron tetrapolyvanadate, vanadyl (IV) sulfate hydrate, vanadium(III) bromide, vanadyl oxalate (oxalic acid oxovanadium(IV) salt), vanadyl(IV) acetate ($VO[OC(O)CH_3]_2$), vanadyl(V) nitrate ($VO(NO_3)_3$), vanadyl glycolate, vanadium hydride, vanadium selenide, vanadium carbide (VC), vanadium nitride (VN), potassium divanadate, potassium vanadate, potassium metavanadate ($KVO_3$), sodium metavanadate ($NaVO_3$), sodium divanadate ($Na_4V_2O_7$), sodium vanadate ($Na_3VO_4$), sodium vanadate hydrate, lithium metavanadate ($LiVO_3$), rubidium divanadate ($Rb_4V_2O_7$), rubidium metavanadate ($RbVO_3$), rubidium vanadate ($Rb_3VO_4$), vanadium diboride, vanadium boride (VB), and vanadium(III) sulfide ($V_2S_3$).

In view of good preservation stability and good ease of handling of the coloring liquid, preferred are vanadyl oxalate, vanadyl nitrate, and vanadyl acetate. The vanadium component may be used alone, or two or more thereof may be used in combination.

A certain preferred embodiment of the present invention is, for example, a coloring liquid comprising a Cr component as a coloring component.

Ions or complexes of Cr may be added in the coloring liquid in the form of salts containing cations and anions of Cr, or in the form of complexes containing Cr and its ligands. Examples of the anions or ligands include $OAc^-$, $NO_3^-$, $NO_2^-$, $CO_3^{2-}$, $HCO_3^-$, $ONC^-$, $SCN^-$, $SO_4^{2-}$, $SO_3^{2-}$, glutarate, lactate, gluconate, propionate, butyrate, glucuronate, benzoate, phenolate, halide anions (fluorides, chlorides, bromides), and acetate.

Specific examples of compounds as Cr components include trivalent and tetravalent compounds. Preferred are trivalent chrome compounds. Examples include chromium (III) chloride, chromium(III) chloride hydrate (hexahydrate), chromium(III) bromide hydrate (hexahydrate), chromium(III) nitrate hydrate (nonahydrate), chromium(III) sulfate hydrate (n-hydrate), chromium(III) acetate hydrate (monohydrate), and chromium(III) formate hydrate (n-hydrate). In view of good solubility in water and in organic solvent, preferred are chromium(III) nitrate hydrate (nonahydrate), chromium(III) chloride hydrate (hexahydrate), and chromium(III) acetate hydrate (monohydrate). The Cr component may be used alone, or two or more thereof may be used in combination.

Preferably, a coloring liquid of the present invention comprises water and/or an organic solvent as solvent. Water and/or an organic solvent allow the organosilicon compound (for example, silicone compound, alkylsilane compound) to dissolve, and improve the penetration of the coloring liquid into a dental ceramic. With the organosilicon compound being dissolved in water, a dental ceramic coloring liquid of the present invention can more easily be applied, and the ease of handling improves. The solvent may be used alone, or two or more thereof may be used in combination.

It is required that water be essentially free of impurities that are detrimental to the effects of the present invention. Preferably, water is purified water, distilled water, ion-exchange water, or deionized water. The content of water in the dental ceramic coloring liquid is preferably 40 to 99.9 mass %, more preferably 42 to 99.7 mass %, even more preferably 45 to 99.5 mass %. Here, "being essentially free of impurities" means that impurities may be present in an amount that does not hinder the effects of the present invention, but not in an amount that hinders the effects of the present invention. The content of impurities may be, for example, less than 0.01 mass %, or less than 0.001 mass %, depending on the type of impurities.

The organic solvent has an SP value of preferably 8.6 $(cal/cm^3)^{1/2}$ or more, more preferably 8.8 $(cal/cm^3)^{1/2}$ or more, as calculated by the method described above. In embodiments containing no coloring component, an SP value of 8.6 $(cal/cm^3)^{1/2}$ or more provides sufficient masking properties by allowing the dissolved organosilicon compound (particularly, hydrophilic silicone compound, hydrophilic alkylsilane compound) to sufficiently penetrate a dental ceramic. In embodiments containing a coloring component, an SP value of 8.6 $(cal/cm^3)^{1/2}$ or more provides sufficient coloring by providing sufficient solubility for the coloring component, and allowing the coloring liquid to sufficiently penetrate a dental ceramic, in addition to providing sufficient masking properties.

Preferably, the organic solvent comprises at least one selected from the group consisting of an alcohol, a glycol, a triol, and a ketone. Specific examples include:

alcohols such as methanol, ethanol, 1-propanol, 2-propanol, isopropanol, 1-butanol, 2-butanol, 1-heptanol, 2-heptanol, 3-heptanol, 1-hexanol, 2-hexanol, 3-hexanol, 2-methyl-1-pentanol, 3-methyl-1-pentanol, 4-methyl-1-pentanol, 2-methyl-2-pentanol, 2-methyl-3-pentanol, 2,2-dimethyl-1-butanol, 2-ethyl-1-butanol, ethylene glycol monomethyl ether, ethylene glycol monoethyl ether, ethylene glycol monobenzyl ether, propylene glycol monomethyl ether, propylene glycol monoethyl ether, ethylene glycol monobutyl ether, diethylene glycol monomethyl ether, diethylene glycol monoethyl ether, diethylene glycol monobenzyl ether, propylene glycol monopropyl ether, tripropylene glycol monomethyl ether, diethylene glycol monobutyl ether, triethylene glycol monomethyl ether, benzyl alcohol, 2-(benzyloxy)ethanol, 3-(benzyloxy)-1-propanol, 2-(benzyloxy)-1-butanol, and 5-(benzyloxy)-1-pentanol;

diols such as 1,2-ethanediol, 1,2-propanediol, 1,3-propanediol, 1,2-butanediol, 1,3-butanediol, 1,4-butanediol, 2,3-butanediol, 1,2-pentanediol, 1,5-pentanediol, 2,4-pentanediol, 1,2-hexanediol, 2,5-hexanediol, ethylene glycol, diethylene glycol, triethylene glycol, tetraethylene glycol, polyethylene glycol (a molecular weight of 200 to 600), propylene glycol, dipropylene glycol, polypropylene glycol, 1-methyl-1,3-propanediol, 2-methyl-1,3-propanediol, 2-methyl-1,4-butanediol, 3-methyl-1,3-butanediol, 2-methyl-2,4-pentanediol, 3-methyl-1,5-pentanediol, 2,4-diethyl-1,5-pentanediol, and 2-ethyl-1,3-hexanediol;

triols such as glycerin, 1,2,4-butanetriol, 1,2,3-butanetriol, and 1,2,6-hexanetriol; and ketones such as acetone, 2-butanone, 2-pentanone, and cyclohexanone.

These organic solvents may be used alone, or two or more thereof may be used in an appropriate combination. The organic solvent may be used as a thickener (described later) to adjust viscosity.

The organic solvent content in a coloring liquid of the present invention is preferably 40 to 99.9 mass %, more preferably 42 to 99.7 mass %, even more preferably to 99.5 mass %.

A certain embodiment is, for example, a dental ceramic coloring liquid that comprises an organosilicon compound (for example, a silicone compound, an alkylsilane compound), a solvent, a complexing agent, and a thickener, and in which the solvent is water and/or an organic solvent, and the solvent content is 40 to 99.7 mass %. In such an embodiment, the solvent content is preferably 41 to 99.6 mass %, more preferably 42 to 99.5 mass %, even more preferably 45 to 99.2 mass %.

In certain embodiments, a coloring liquid of the present invention (for example, a coloring liquid containing a silicone compound, or a coloring liquid containing an alkylsilane compound) has a pH of preferably 0 to 12, more preferably 1 to 11, even more preferably 2 to 10. A wide range of pH is applicable because the organosilicon compound contained in the present invention has good preservation stability, and is not susceptible to the effect of pH. With a pH falling outside of these ranges, the silicone compound or coloring component may start precipitating from the solution. The pH can be measured with a commercially available pH meter (for example, a compact pH meter LAQUAtwin manufactured by Horiba Ltd.).

A coloring liquid of the present invention may comprise a complexing agent to such an extent that it does not hinder the effects of the present invention. Adding a complexing agent may be beneficial in improving the storage stability of the coloring component in the coloring liquid, accelerating the dissolution process of the salts added to the coloring liquid, and/or increasing the amount of salts that can dissolve in the coloring liquid.

The complexing agent can typically form complexes with the metal ions present in the coloring liquid. The complexes formed must be soluble in solvent. For example, the complexing agent may be used in at least a stoichiometric proportion in relation to the molar quantity of the ions of the coloring component contained in the coloring liquid. Desirable results can be obtained when the mole ratio of the complexing agent is about 1 or about 2, or about 3 or more relative to the cations in the coloring liquid.

Examples of the complexing agent include N,N-di(2-hydroxyethyl)glycine, acetylacetonate, crown ether, cryptands, ethylenediaminetriacetate and salts thereof, ethylenediaminetetraacetate and salts thereof, nitrilotriacetate and salts thereof, citric acid and salts thereof, triethylenetetramine, porphin, polyacrylate, polyasparate, acidic peptides, phthalocyanine, salicylate, glycinate, lactate, propylenediamine, ascorbate, oxalic acid and salts thereof, and a mixture of these. The complexing agent may be used alone, or two or more thereof may be used in an appropriate combination.

The content of the complexing agent in a coloring liquid of the present invention is not particularly limited, as long as the present invention can exhibit its effects. For example, it is preferable to contain the complexing agent in an amount sufficient to dissolve the cations in the solution, or to prevent precipitation of the cations. Specifically, the content of the complexing agent in the coloring liquid is preferably 0.01 mass % or more, more preferably 0.05 mass % or more, even more preferably 0.10 mass % or more. There is no specific upper limit for the content of the complexing agent. However, the content of the complexing agent is preferably 50 mass % or less, more preferably 20 mass % or less, even more preferably 10 mass % or less. The complexing agent may fail to fully dissolve the cations when used in excessively small amounts, whereas the excess portion of the complexing agent itself may remain without dissolving when the complexing agent is used in excessively large amounts.

Preferably, a coloring liquid of the present invention has an appropriate viscosity so that the coloring liquid, in addition to being applied to a ceramic surface in necessary amounts, can move into the pores of a ceramic unfired body or a ceramic pre-sintered body. The appropriate viscosity is, for example, preferably 0.1 to 10,000 mPa, more preferably 0.5 to 6,000 mPa, even more preferably 1 to 3,000 mPa at 20° C. When the viscosity is too high, it may not be possible to contain the coloring liquid in the pores of a ceramic unfired body or a ceramic pre-sintered body. The viscosity can be measured at 25° C. with a Brookfield viscometer, though the method of viscosity measurement is not particularly limited.

In order to achieve the appropriate viscosity, a coloring liquid of the present invention may comprise one or more thickeners to such an extent that it does not hinder the effects of the present invention.

The thickener may be selected from the above organic solvents to adjust viscosity, or may be selected from the following thickeners. Examples of thickeners other than the organic solvents include:

polysaccharide compounds such as methyl cellulose, carboxycellulose, hydroxyethyl cellulose, xanthan gum, guar gum, carrageenan, tamarind seed gum, and pectin;

sugar alcohol compounds such as sorbitol, erythritol, xylitol, and trehalose;

synthetic polyol compounds such as diglycerin, triglycerin, polyglycerin, and polyvinyl alcohol; and solid organic compounds such as sodium polyacrylate, ammonium polyacrylate, polyethylene oxide, polyethylene glycol (a molecular weight of 1,000 or more), polyvinylpyrrolidone, calcium stearate, magnesium stearate, zinc stearate, aluminum stearate, polyethylene glycol monostearate, 12-hydroxystearic acid, stearamide, oleamide, and ethylenebisoleamide. These thickeners may be used alone, or two or more thereof may be used in an appropriate combination.

The content of the thickener in a coloring liquid of the present invention is preferably 0.01 to 10 mass %, more preferably 0.1 to 8 mass %, even more preferably 0.2 to 5 mass %.

A coloring liquid of the present invention may comprise other additives and other masking agents, provided that it does not hinder the effects of the present invention.

Examples of such other additives include stabilizers (for example, methoxyphenol, hydroquinone, Topanol A (such as 2,4-dimethyl-6-tert-butylphenol), and a mixture of these (excluding a stabilizer capable of reducing a phase transformation of zirconia)), buffers (for example, acetate, amino buffer, and a mixture of these), antimicrobial agents (for example, gluconates such as chlorhexidine gluconate), preservatives (for example, sorbic acid, benzoic acid, and a mixture of these), silane compounds, and a mixture of these. Examples of the additional masking agents include nitrates (such as aluminum nitrate), phosphorus components (such as phosphoric acid), sodium silicate pentahydrate, water-soluble aluminum compounds, and water-soluble lanthanum compounds. The additional additives and additional masking agents may be used alone, or two or more thereof may be used in combination. The content of these additives and masking agents in a coloring liquid of the present invention may be, for example, 0.01 to 10 mass %, 0.05 to 5 mass %, or 0.1 to 3 mass %.

A dental ceramic coloring liquid of the present invention may comprise other components, provided that the present invention can exhibit its effects. Examples of such other components include phosphorus-containing components such as phosphoric acid, phosphates (e.g., ammonium salts), and phosphoric acid esters; nitrates such as potassium nitrate, magnesium nitrate, cobalt(II) nitrate, nickel(II) nitrate, praseodymium(III) nitrate, cerium(III) nitrate, and neodymium(III) nitrate; chlorides such as erbium chloride, yttrium chloride, and iron chloride; water-soluble aluminum compounds (e.g., aluminum nitrate); and water-soluble lanthanum compounds. The content of the additional components may be, for example, less than 10 mass %, less than 5 mass %, less than 1 mass %, or less than 0.01 mass %. A certain preferred embodiment is, for example, a dental ceramic coloring liquid that does not contain such additional components. By being used in place of dental porcelain, a dental ceramic coloring liquid of the present invention can mask the influence of an underlying color such as discoloration of remaining teeth, or the color of a metallic dental prosthesis such as an implant abutment or a metal core, which cannot be achieved with dental porcelain unless it is laminated in multiple layers. To this end, in certain preferred embodiments, a dental ceramic coloring liquid of the present invention does not comprise a glass component (such as $SiO_2$, $Al_2O_3$, $Li_2O$, $Na_2O$, or $K_2O$) contained in dental porcelain. It is, however, possible to combine a dental ceramic coloring liquid of the present invention with dental porcelain to provide a dental prosthesis having even better aesthetics.

A dental ceramic colored with a coloring liquid of the present invention is not particularly limited, as long as it contains a ceramic used in dentistry. Examples include those containing, for example, zirconia (zirconium oxide or $ZrO_2$ as it is also called), alumina (aluminum oxide or $Al_2O_3$ as it is also called), feldspar glass, disilicate glass, or porcelain. Preferred as dental ceramics are those containing zirconia and/or alumina, more preferably those containing zirconia as a main component. Here, "main component" is as described below in conjunction with zirconia pre-sintered body.

A dental ceramic colored with a coloring liquid of the present invention may be an unfired body or a pre-sintered body, provided that it is not sintered. However, in view of penetration of the coloring liquid, a zirconia pre-sintered body is preferred in the case of a dental ceramic containing zirconia as a main component.

Another embodiment of the present invention is, for example, a dental ceramic (a colored ceramic pre-sintered body or a colored unfired body) supporting an organosilicon compound (for example, a silicone compound, an alkylsilane compound) on a surface of the dental ceramic. The content of the organosilicon compound is not particularly limited, as long as the present invention can exhibit its effects. For example, the content of the organosilicon compound can be appropriately adjusted by adjusting the applied amount of a coloring liquid of the present invention, according to, for example, the desired intensity of masking properties to be obtained after sintering. The organosilicon compound can be adjustably supported not only on the outermost surface but in the surface of a ceramic pre-sintered body or unfired body because the organosilicon compound can penetrate into a ceramic pre-sintered body or unfired body by capillary action through spaces that are in communication with outside, following application of, for example, a coloring liquid of the present invention. By "support", it generally means a state of adhesion to a support. In the present invention, "support" refers to a state of adhesion to a ceramic by means of, for example, adsorption.

With a dental ceramic of the present invention, the desired masking properties needed for dental use can be imparted after firing, while imparting a desired color at the same time when a coloring component is contained. An example of such an embodiment is a dental ceramic supporting a coloring component. The coloring component is as described in conjunction with the coloring liquid.

Preferably, the ceramic pre-sintered body or unfired body comprises zirconia as a main component, as noted above. Below is a description of an embodiment in which the dental ceramic comprises zirconia as a main component. In the present invention, a pre-sintered body after coloring is called "colored ceramic pre-sintered body" or "colored zirconia pre-sintered body" to distinguish it from "ceramic pre-sintered body" or "zirconia pre-sintered body", a simplified term used herein to refer to a pre-sintered body before coloring with the coloring liquid. A coloring liquid of the present invention can also be used to color a zirconia unfired body. In this case, a zirconia sintered body is produced without producing a pre-sintered body. In situations assuming such sintered bodies, the conditions in the descriptions given below in conjunction with zirconia pre-sintered bodies are equally applicable as preferred embodiments of the zirconia unfired body. The ceramic pre-sintered body and unfired body may have, for example, a block or disc shape.

The following describes a zirconia pre-sintered body of the present invention. The zirconia pre-sintered body refers to a material containing zirconia ($ZrO_2$: zirconium oxide) as a main component, and in which zirconia has pre-sintered (a state where zirconia particles (powder) are not fully sintered). The zirconia pre-sintered body may be one that has been shaped according to the dental product to be produced. The main component may be 50 mass % or more. The zirconia content in a zirconia pre-sintered body according to the present invention is preferably 60 mass % or more, more preferably 65 mass % or more, even more preferably 70 mass % or more, yet more preferably 75 mass % or more, particularly preferably 80 mass % or more, most preferably 85 mass % or more. For example, for applications as dental prostheses or dental implant products, the zirconia pre-sintered body can be prepared by, for example, pre-sintering a disc or a block obtained by press forming a zirconia powder using a known technique. The zirconia content in the zirconia unfired body is the same as that in the zirconia pre-sintered body. The zirconia pre-sintered body has a density of preferably 2.7 g/cm$^3$ or more. The zirconia pre-sintered body has a density of preferably 4.0 g/cm$^3$ or less, more preferably 3.8 g/cm$^3$ or less, even more preferably 3.6 g/cm$^3$ or less. Molding can be performed with ease when the density is confined in these ranges. The density of the pre-sintered body can be calculated as, for example, a ratio of the mass of the pre-sintered body to the volume of the pre-sintered body. The zirconia pre-sintered body has a three-point flexural strength of preferably 15 to 70 MPa, more preferably 18 to 60 MPa, even more preferably 20 to 50 MPa. The flexural strength can be measured following ISO 6872:2015 except for the specimen size, using a specimen measuring 5 mm in thickness, 10 mm in width, and 50 mm in length. For surface finishing, the specimen surfaces, including chamfered surfaces (45° chamfers at the corners of specimen), are finished longitudinally with #600 sandpaper. The specimen is disposed in such an orientation that its widest face is perpendicular to the vertical direction (loading direction). In the flexure test, measurements are made at a span of 30 mm with a crosshead speed of 0.5 mm/min.

Preferably, a zirconia pre-sintered body of the present invention comprises a stabilizer capable of reducing a phase transformation of zirconia (hereinafter, also referred to simply as "stabilizer"). For example, a stabilizer is preferably contained in zirconia before pre-sintering.

Examples of the stabilizer include oxides such as yttrium oxide ($Y_2O_3$; hereinafter "yttria"), calcium oxide (CaO), magnesium oxide (MgO), cerium oxide ($CeO_2$), scandium oxide ($Sc_2O_3$), niobium oxide ($Nb_2O_5$), lanthanum oxide ($La_2O_3$), erbium oxide ($Er_2O_3$), praseodymium oxide ($Pr_6O_{11}$), samarium oxide ($Sm_2O_3$), europium oxide ($Eu_2O_3$), and thulium oxide ($Tm_2O_3$). Preferred is yttria. These may be used alone, or two or more thereof may be used in combination. In a certain preferred embodiment of the coloring liquid, a dental ceramic to be colored contains zirconia as a main component, and yttria as a stabilizer, and the stabilizer consists essentially of yttria. In such a preferred embodiment, "stabilizer consisting essentially of yttria" means that the content of stabilizers other than yttria is less than 0.1 mol %, preferably 0.05 mol % or less, more preferably 0.01 mol % or less, even more preferably 0.001 mol % or less in total 100 mol % of zirconia and stabilizer. The stabilizer content can be measured, for example, by inductively coupled plasma (ICP) emission spectral analysis or X-ray fluorescence analysis.

When the dental ceramic is containing zirconia as a main component, and additionally containing a stabilizer, the stabilizer content is preferably 0.1 to 18 mol %, more preferably 1 to 15 mol %, even more preferably 1.5 to 10 mol % in total 100 mol % of zirconia and stabilizer. The type and content of the stabilizer in a zirconia unfired body are the same as in a zirconia pre-sintered body. In certain preferred embodiments, the yttria content in a dental ceramic containing zirconia as a main component is preferably 2.5 to 9.5 mol %, more preferably 3.0 to 9.0 mol %, even more preferably 3.5 to 8.5 mol % in total 100 mol % of zirconia and stabilizer.

A zirconia unfired body and zirconia pre-sintered body of the present invention may optionally comprise, for example, a colorant (including a pigment, a composite pigment, and a fluorescent agent), alumina ($Al_2O_3$), titanium oxide ($TiO_2$), or silica ($SiO_2$). These components may be used alone, or two or more thereof may be used as a mixture. Examples of the pigment include an oxide of at least one component selected from the group consisting of Ti, V, Cr, Mn, Fe, Co, Ni, Zn, Y, Zr, Sn, Sb, Bi, Ce, Pr, Sm, Eu, Gd, Tb, and Er. Examples of the composite pigment include $(Zr,V)O_2$, $Fe(Fe,Cr)_2O_4$, $(Ni,Co,Fe)(Fe,Cr)_2O_4ZrSiO_4$, and $(Co,Zn)Al_2O_4$. Examples of the fluorescent agent include $Y_2SiO_5$:Ce, $Y_2SiO_5$:Tb, $(Y,Gd,Eu)BO_3$, $Y_2O_3$:Eu, YAG:Ce, $ZnGa_2O_4$:Zn, and $BaMgAl_{10}O_{17}$:Eu.

A typical method of production of a zirconia pre-sintered body of the present invention is as follows. First, raw material granules of zirconia containing a stabilizer are prepared, and the granules are pressed into a shape such as a block or a disc. Optionally, the molded body (unfired body) is subjected to CIP (Cold Isostatic Pressing). The applied pressure is, for example, 50 to 500 MPa. This is followed by pre-sintering. Pre-sintering can produce a zirconia pre-sintered body by gradually increasing temperature from room temperature to 800 to 1,200° C., and retaining the temperature for about 1 to 6 hours. The resulting zirconia pre-sintered body can then be milled with a known device, according to the final dental product. For example, when the dental product is a dental prosthesis, the zirconia pre-sintered body is milled into a shape of a dental cap with a CAD/CAM or other device.

A method of production of a colored zirconia pre-sintered body of the present invention comprises the step of containing the dental ceramic coloring liquid in a zirconia pre-sintered body after milling. The dental ceramic coloring liquid may be contained by, for example, being applied to the zirconia pre-sintered body with a brush or the like, dipping the zirconia pre-sintered body in a container containing the coloring liquid, or spraying the coloring liquid to the zirconia pre-sintered body with a sprayer or the like. Known tools and devices can be used. When a zirconia sintered body is produced directly from an unfired body without the pre-sintering step, the dental ceramic coloring liquid may be contained in the zirconia unfired body after milling.

The present invention also encompasses a zirconia sintered body obtained by sintering the colored zirconia pre-sintered body. A method of production of the zirconia sintered body comprises the step of firing the colored zirconia pre-sintered body. The firing temperature (highest temperature in firing) can be appropriately selected according to the type of zirconia, and is not particularly limited as long as the coloring component can develop color. However, the firing temperature is preferably 1,350° C. or more, more preferably 1,450° C. or more, even more preferably 1,500° C. or more. The upper limit of firing temperature is not particularly limited, and is, for example, preferably 1,600° C. or less. A zirconia sintered body of the present invention encompasses not only sintered bodies after sintering of molded zirconia powder under ordinary pressure or no applied pressure, but sintered bodies compacted by a high-temperature pressing process such as HIP (Hot Isostatic Pressing).

The stabilizer content in a zirconia sintered body and zirconia pre-sintered body of the present invention can be measured, for example, by inductively coupled plasma (ICP) emission spectral analysis or X-ray fluorescence analysis.

Preferably, a zirconia sintered body of the present invention has at least one of partially stabilized zirconia and fully stabilized zirconia as the matrix phase. In the zirconia sintered body, the predominant crystalline phase of zirconia is at least one of the tetragonal crystal system and the cubic crystal system. The zirconia sintered body may have both the tetragonal crystal system and the cubic crystal system. Preferably, the zirconia sintered body is essentially free of a monoclinic crystal system. Zirconia that is partially stabilized by addition of a stabilizer is called partially stabilized zirconia (PSZ), whereas zirconia that is fully stabilized is called fully stabilized zirconia.

The present invention encompasses dental products formed from the zirconia sintered body. Examples of the dental products include dental prostheses, orthodontic products, and dental implant products. The dental prostheses can be used as, for example, zirconia inlays, onlays, laminate veneers, or crowns.

In the foregoing embodiments, aspects such as the type and content of each component can be changed as appropriate, and changes such as additions and deletions can be made in any of the components. In the foregoing embodiments, the composition and property values of the coloring liquid can be varied and combined as appropriate.

The present invention encompasses embodiments combining the foregoing features, provided that the present invention can exhibit its effects with such combinations made in various forms within the technical idea of the present invention.

EXAMPLES

The following describes the present invention in greater detail by way of Examples. The present invention, however, is not limited by the following descriptions.

Examples 1-1 to 1-24, Examples 2-1 to 2-18, and Comparative Examples 1-1 to 1-6

Coloring liquids were prepared for Examples and Comparative Examples, and their properties were evaluated, as follows. The results are presented in Tables 1 to 4.

Method of Evaluation of Solubility of Organosilicon Compound in Water

Water (pH 7) was added to 0.015 g of organosilicon compound in an amount of 2.985 g, and to 0.15 g of organosilicon compound in an amount of 2.85 g. The mixtures were visually observed after being stirred at 25° C. for 1 hour, and the solubility was evaluated according to the following criteria.

A: Solubility in water is 5 mass % or more at 25° C.

B: Solubility in water is 0.5 mass % or more and less than 5 mass % at 25° C.

C: Solubility in water is less than 0.5 mass % at 25° C.

Preparation of Coloring Liquid

The components shown in Tables 1 to 4 were mixed at ordinary temperature in the mass percentages shown in the Tables to prepare coloring liquids. The following organosilicon compounds were used. The solubility in water was evaluated using the criteria below.

Silicone Compounds

KP-120: Polyether-modified silicone manufactured by Shin-Etsu Chemical Co., Ltd.; SP value: 10.0 $(cal/cm^3)^{1/2}$; solubility in water: A KP-106: Polyether-modified silicone manufactured by Shin-Etsu Chemical Co., Ltd.; SP value: 8.9 $(cal/cm^3)^{1/2}$; solubility in water: A KP-110: Polyether-modified silicone manufactured by Shin-Etsu Chemical Co., Ltd.; SP value: 8.3 $(cal/cm^3)^{1/2}$; solubility in water: B KP-104: Polyol-modified silicone manufactured by Shin-Etsu Chemical Co., Ltd.; SP value: 11.6 $(cal/cm^3)^{1/2}$; solubility in water: A

Alkylsilane Compounds

KBM-403: 3-Glycidoxypropyltrimethoxysilane manufactured by Shin-Etsu Chemical Co., Ltd.; solubility in water: A KBM-602: N-2-(Aminoethyl)-3-aminopropylmethyldimethoxysilane manufactured by Shin-Etsu Chemical Co., Ltd.; solubility in water: A KBM-903: 3-Aminopropyltrimethoxysilane manufactured by Shin-Etsu Chemical Co., Ltd.; solubility in water: A Trimethylsilanol: manufactured by Shin-Etsu Chemical Co., Ltd.; solubility in water: B

Evaluation of Preservation Stability of Coloring Liquid

The coloring liquid (12 ml) prepared in the manner described above was filled into a container for ES liquid (manufactured by Kuraray Noritake Dental Inc.), and was stored at 40° C., 50° C., and 60° C. for 60 days by reflecting the actual environment of use of coloring liquid, including delivery and storage. After storage, the coloring liquid was evaluated according to the following criteria.

Good: No visually observable separation of coloring liquid components or gelation of coloring liquid Poor: Separation of coloring liquid components, or gelation of coloring liquid is visually observable

Production of Zirconia Pre-Sintered Body

The following describes the method of production of a zirconia pre-sintered body to which the coloring liquid is applied.

First, a zirconia powder containing a stabilizer was prepared. A mixture was prepared by adding 9.9 mass % (5.5 mol %) of yttria as stabilizer to 90.1 mass % of a zirconia powder. The mixture was added to water to prepare a slurry, and the slurry was mixed and pulverized to an average particle diameter of 0.13 μm or less by wet pulverization with a ball mill. After pulverization, the slurry was dried with a spray dryer, and the resulting powder was fired at 950° C. for 2 hours to prepare a powder (primary powder). The average particle diameter can be determined by a laser diffraction scattering method. As a specific example of a laser diffraction scattering method, a 0.2% aqueous solution of sodium hexametaphosphate may be used as a dispersion medium for the measurement of average particle diameter by volume, using a laser diffraction particle size distribution analyzer (SALD-2300, manufactured by Shimadzu Corporation).

Water was added to the primary powder to prepare a slurry, and the slurry was mixed and pulverized to an average particle diameter of 0.13 μm or less by wet pulverization with a ball mill. After adding a binder to the pulverized slurry, the slurry was dried with a spray dryer to prepare a powder (secondary powder). The secondary powder was used as a raw material powder for the production of the zirconia pre-sintered body below.

The method of production of a zirconia pre-sintered body is as follows. The raw material powder (1.32 g) was filled into a die measuring 19 mm in diameter, and was pressed under a surface pressure of 57.5 kN for 20 seconds with a uniaxial pressing machine (primary press forming). The resulting primary press-molded body was then fired at 1,000° C. for 2 hours to prepare a zirconia pre-sintered body.

Measurement of Chromaticity of Sintered Body

The coloring liquid prepared was applied to the zirconia pre-sintered body with a brush, and the zirconia pre-sintered body was fired into a zirconia sintered body under the firing conditions shown in Tables 1 to 4. The zirconia sintered body was ground into a circular disc measuring 15 mm in diameter and 1.2 mm in thickness, and was measured for chromaticity against a white background according to L*a*b*color system (JIS Z 8781-4:2013 Color Measurements—Part 4: CIE 1976 L*a*b* color space), using a spectrophotometer (Crystaleye; measurement mode: 7-band LED light source) manufactured by Olympus Corporation (n=3). Tables 1 to 4 show the mean values of measured values. Chroma ($C^*=((a^*)^2+(b^*)^2)^{1/2}$) was calculated from the measured mean values of a* and b*.

Measurement of Transparency of Sintered Body

The coloring liquid prepared was applied to the zirconia pre-sintered body with a brush, and the zirconia pre-sintered body was fired into a sintered body under the firing conditions shown in Tables 1 to 4. The sintered body was ground into a circular disc measuring 15 mm in diameter and 1.2 mm in thickness, and was measured for chromaticity using a spectrophotometer (Crystaleye; measurement mode: 7-band LED light source) manufactured by Olympus Corporation. In the chromaticity measurement, the same specimen was measured for lightness (Lw*) against a white background, and lightness (Lb*) against a black background, using the same measurement device in the same measurement mode with the same light source. The difference ($\Delta L^*=(Lw^*)-(Lb^*)$) was then determined as transparency ($\Delta L^*$) (n=3). Tables 1 to 4 show the mean values of calculated values. Separately, the percentage change of transparency was calculated using the following formula, relative to the zirconia sintered body that was not colored with a coloring liquid (Comparative Example 1-1).

Percentage change of transparency (%)={(transparency of sintered body fired after application of coloring liquid−transparency of uncolored zirconia sintered body)/transparency of uncolored zirconia sintered body}×100

Evaluation of Sintered Body for Degree of Masking

The zirconia pre-sintered body produced was milled into a crown shape using a dental milling machine (DWX-51D manufactured by Roland DG under this trade name), and the coloring liquid prepared was applied to inside of the crown shape with a brush. The zirconia pre-sintered body was then fired into a sintered body under the firing conditions shown in Tables 1 to 4. The crown-shaped sintered body was placed over a metallic abutment tooth, and the degree of masking was evaluated using the following criteria.

Good: The color of metallic abutment tooth is not visible through the sintered body compared to the sintered body with no application of coloring liquid (a high degree of masking).

Moderate: The color of metallic abutment tooth is visible, but only slightly compared to the sintered body with no application of coloring liquid (a moderately high degree of masking).

Poor: The color of metallic abutment tooth is visible, or as visible as that seen through the sintered body with no application of coloring liquid (a low degree of masking, or no masking).

Measurement of Biaxial Flexural Strength of Sintered Body

The coloring liquid prepared was applied to the zirconia pre-sintered body with a brush, and the zirconia pre-sintered body was fired into a sintered body (15 mm in diameter, 1.2 mm in thickness) under the firing conditions shown in Tables 1 to 4. The sintered body was measured for biaxial flexural strength in compliance with JIS T 6526:2012 at a crosshead speed of 0.5 mm/min, using a universal precision tester Autograph (AG-I 100 kN) manufactured by Shimadzu Corporation under this trade name (n=3). Tables 1 to 4 show the mean values of measured values. Separately, the percentage change of biaxial flexural strength was calculated using the following formula, relative to the zirconia sintered body that was not colored with a coloring liquid (Comparative Example 1-1).

Percentage change of biaxial flexural strength (%)={(biaxial flexural strength of sintered body fired after application of coloring liquid−biaxial flexural strength of uncolored zirconia sintered body)/biaxial flexural strength of uncolored zirconia sintered body}×100

TABLE 1

| Components (mass %) | | Ex. 1-1 | Ex. 1-2 | Ex. 1-3 | Ex. 1-4 | Ex. 1-5 | Ex. 1-6 | Ex. 1-7 |
|---|---|---|---|---|---|---|---|---|
| Silicone compound | KP-120 | 1.00 | 5.00 | 10.0 | 50.0 | 5.00 | 10.0 | 50.0 |
| | KP-106 | | | | | | | |
| | KP-110 | | | | | | | |
| | KP-104 | | | | | | | |
| Coloring component | Chromium(III) acetate | | | | | 0.100 | 0.100 | 0.100 |
| | Vanadyl(IV) oxalate | | | | | 0.100 | 0.100 | 0.100 |
| Solvent | Purified water | 99.0 | 95.0 | 90.0 | 50.0 | 94.8 | 89.8 | 49.8 |
| | Ethanol | | | | | | | |
| | Propylene glycol | | | | | | | |
| | Propylene glycol monomethyl ether | | | | | | | |
| | Acetone | | | | | | | |

TABLE 1-continued

| | | | | | | | | |
|---|---|---|---|---|---|---|---|---|
| Thickener | Xanthan gum | | | | | | | |
| Complexing agent | N,N-Di(2-hydroxyethyl)glycine | | | | | | | |
| Other masking agent | Sodium silicate pentahydrate | | | | | | | |
| | Phosphoric acid | | | | | | | |
| | Aluminum nitrate | | | | | | | |
| Preservation stability of coloring liquid | 40° C., 60 days | Good | Good | Good | Good | Good | Good | Good |
| | 50° C., 60 days | Good | Good | Good | Good | Good | Good | Good |
| | 60° C., 60 days | Good | Good | Good | Good | Good | Good | Good |
| Firing temperature (° C.)[*1] | | 1550 | 1550 | 1550 | 1550 | 1550 | 1550 | 1550 |
| Shade after firing | L* | 92.51 | 92.91 | 93.29 | 93.60 | 82.12 | 83.60 | 88.96 |
| | a* | −2.03 | −1.70 | −1.68 | −1.84 | 1.85 | 1.91 | −2.17 |
| | b* | 4.10 | 3.37 | 2.86 | 3.44 | 14.67 | 15.41 | 8.98 |
| | Chroma C* | 4.58 | 3.77 | 3.32 | 3.90 | 14.79 | 15.53 | 9.24 |
| Transparency ΔL* of zirconia sintered body | | 7.86 | 6.04 | 4.35 | 3.53 | 2.37 | 1.12 | 1.91 |
| Percentage change of transparency (%) | | −51.4 | −62.6 | −73.1 | −78.2 | −85.4 | −93.1 | −88.2 |
| Visual degree of masking with zirconia sintered body | | Good | Good | Good | Good | Good | Good | Good |
| Visual shade of zirconia sintered body | | White | White | White | White | Pale yellow | Pale yellow | Pale yellow |
| Biaxial flexural strength of zirconia sintered body (MPa) | | 668 | 680 | 681 | 691 | 698 | 685 | 681 |
| Percentage change of biaxial flexural strength (%) | | 3.2 | 5.1 | 5.3 | 6.8 | 7.9 | 5.9 | 5.3 |

| Components (mass %) | | Ex. 1-8 | Ex. 1-9 | Ex. 1-10 | Ex. 1-11 | Ex. 1-12 | Ex. 1-13 | Ex. 1-14 | Ex. 1-15 |
|---|---|---|---|---|---|---|---|---|---|
| Silicone compound | KP-120 | | | | | | | | |
| | KP-106 | 10.0 | 50.0 | 10.0 | | | | | |
| | KP-110 | | | | 0.500 | | | | |
| | KP-104 | | | | | 0.300 | 1.50 | 3.00 | 9.00 |
| Coloring component | Chromium(III) acetate | | | 0.100 | 0.100 | | | | |
| | Vanadyl(IV) oxalate | | | 0.100 | 0.100 | | | | |
| Solvent | Purified water | 90.0 | 50.0 | 89.8 | 99.3 | 99.0 | 95.0 | 90.0 | 70.0 |
| | Ethanol | | | | | | | | |
| | Propylene glycol | | | | | | | | |
| | Propylene glycol monomethyl ether | | | | | 0.700 | 3.50 | 7.00 | 21.0 |
| | Acetone | | | | | | | | |
| Thickener | Xanthan gum | | | | | | | | |
| Complexing agent | N,N-Di(2-hydroxyethyl)glycine | | | | | | | | |
| Other masking agent | Sodium silicate pentahydrate | | | | | | | | |
| | Phosphoric acid | | | | | | | | |
| | Aluminum nitrate | | | | | | | | |
| Preservation stability of coloring liquid | 40° C., 60 days | Good | Good | Good | Good | Good | Good | Good | Good |
| | 50° C., 60 days | Good | Good | Good | Good | Good | Good | Good | Good |
| | 60° C., 60 days | Good | Good | Good | Good | Good | Good | Good | Good |
| Firing temperature (° C.)[*1] | | 1550 | 1550 | 1550 | 1550 | 1550 | 1550 | 1550 | 1550 |
| Shade after firing | L* | 92.79 | 93.15 | 87.56 | 86.24 | 90.99 | 92.91 | 91.27 | 93.51 |
| | a* | −1.87 | −2.10 | 3.60 | −4.03 | −2.40 | −1.70 | −1.75 | −1.80 |
| | b* | 4.01 | 3.88 | 14.87 | 16.24 | 6.11 | 3.37 | 3.51 | 3.78 |
| | Chroma C* | 4.42 | 4.41 | 15.30 | 16.73 | 6.57 | 3.77 | 3.92 | 4.19 |
| Transparency ΔL* of zirconia sintered body | | 7.26 | 4.30 | 1.43 | 9.54 | 9.94 | 5.19 | 4.66 | 2.48 |
| Percentage change of transparency (%) | | −55.1 | −73.4 | −91.2 | −41.0 | −38.6 | −67.9 | −71.2 | −84.7 |
| Visual degree of masking with zirconia sintered body | | Good | Good | Good | Moderate | Moderate | Good | Good | Good |
| Visual shade of zirconia sintered body | | White | White | Pale yellow | Pale yellow | White | White | White | White |
| Biaxial flexural strength of zirconia sintered body (MPa) | | 683 | 689 | 691 | 659 | 641 | 653 | 678 | 675 |
| Percentage change of biaxial flexural strength (%) | | 5.6 | 6.5 | 6.8 | 1.9 | -0.9 | 0.9 | 4.8 | 4.3 |

[*1] In the Table, "Firing temperature" means the highest temperature in firing. Conditions other than firing temperature: Temperature increase from room temperature to 1,550° C. at 10° C./min; retention at 1,550° C. for 2 hours; temperature decrease at −10° C./min and left to cool from 300° C. to room temperature.

TABLE 2

| Components (mass %) | | Ex. 1-16 | Ex. 1-17 | Ex. 1-18 | Ex 1-19 | Ex. 1-20 | Ex. 1-21 | Ex. 1-22 | Ex. 1-23 | Ex. 1-24 |
|---|---|---|---|---|---|---|---|---|---|---|
| Silicone compound | KP-120 | | | | | 10.0 | 10.0 | 10.0 | 10.0 | 10.0 |
| | KP-106 | | | | | | | | | |
| | KP-110 | | | | | | | | | |
| | KP-104 | 30.0 | 3.00 | 15.0 | 30.0 | | | | | |
| Coloring component | Chromium(III) acetate | | 0.100 | 0.100 | 0.100 | 0.100 | 0.100 | 0.100 | 0.100 | 0.100 |
| | Vanadyl(IV) oxalate | | 0.100 | 0.100 | 0.100 | 0.100 | 0.100 | 0.100 | 0.100 | 0.100 |
| Solvent | Purified water | | 89.8 | 49.8 | | 10.0 | 10.0 | 10.0 | 89.5 | 89.7 |
| | Ethanol | | | | | 79.8 | | | | |
| | Propylene glycol | | | | | | 79.8 | | | |
| | Propylene glycol monomethyl ether | 70.0 | 7.00 | 35.0 | 69.8 | | | | | |
| | Acetone | | | | | | | 79.8 | | |

TABLE 2-continued

| | | | | | | | | | | |
|---|---|---|---|---|---|---|---|---|---|---|
| Thickener | Xanthan gum | | | | | | | | 0.300 | |
| Complexing agent | N,N-Di(2-hydroxyethyl)glycine | | | | | | | | | 0.100 |
| Other masking agent | Sodium silicate pentahydrate | | | | | | | | | |
| | Phosphoric acid | | | | | | | | | |
| | Aluminum nitrate | | | | | | | | | |
| Preservation stability of coloring liquid | 40° C., 60 days | Good | Good | Good | Good | Good | Good | Good | Good | Good |
| | 50° C., 60 days | Good | Good | Good | Good | Good | Good | Good | Good | Good |
| | 60° C., 60 days | Good | Good | Good | Good | Good | Good | Good | Good | Good |
| Firing temperature (° C.)[*1] | | 1550 | 1550 | 1550 | 1550 | 1550 | 1550 | 1550 | 1550 | 1550 |
| Shade after firing | $L^*$ | 93.86 | 82.87 | 84.61 | 92.03 | 83.71 | 83.34 | 83.91 | 83.21 | 83.51 |
| | $a^*$ | −1.80 | 1.88 | −1.59 | −3.24 | 1.89 | 1.78 | 1.91 | 1.73 | 1.81 |
| | $b^*$ | 3.18 | 16.31 | 9.31 | 8.85 | 15.51 | 15.21 | 15.73 | 15.04 | 15.45 |
| | Chroma $C^*$ | 3.65 | 16.42 | 9.45 | 9.42 | 15.62 | 15.31 | 15.85 | 15.14 | 15.56 |
| Transparency ΔL* of zirconia sintered body | | 2.71 | 1.07 | 1.27 | 2.31 | 1.23 | 1.17 | 1.25 | 1.15 | 1.21 |
| Percentage change of transparency (%) | | −83.3 | −93.4 | −92.2 | −85.7 | −92.4 | −92.8 | −92.3 | −92.9 | −92.5 |
| Visual degree of masking with zirconia sintered body | | Good | Good | Good | Good | Good | Good | Good | Good | Good |
| Visual shade of zirconia sintered body | | White | Pale yellow | Pale yellow | Pale yellow | Pale yellow | Pale yellow | Pale yellow | Pale yellow | Pale yellow |
| Biaxial flexural strength of zirconia sintered body (MPa) | | 685 | 676 | 665 | 679 | 679 | 692 | 683 | 681 | 689 |
| Percentage change of biaxial flexural strength (%) | | 5.9 | 4.5 | 2.8 | 4.9 | 4.9 | 7.0 | 5.6 | 5.3 | 6.5 |

| Components (mass %) | | Com. Ex. 1-1 | Com. Ex. 1-2 | Com. Ex. 1-3 | Com. Ex. 1-4 | Com. Ex. 1-5 | Com. Ex. 1-6 |
|---|---|---|---|---|---|---|---|
| Silicone compound | KP-120 | No application of coloring liquid | | | | | |
| | KP-106 | | | | | | |
| | KP-110 | | | | | | |
| | KP-104 | | | | | | |
| Coloring component | Chromium(III) acetate | | | 0.100 | | | |
| | Vanadyl(IV) oxalate | | | 0.100 | | | |
| Solvent | Purified water | | 90.0 | 89.8 | 90.0 | 90.0 | 70.0 |
| | Ethanol | | | | | | |
| | Propylene glycol | | | | | | |
| | Propylene glycol monomethyl ether | | | | | | |
| | Acetone | | | | | | |
| Thickener | Xanthan gum | | | | | | |
| Complexing agent | N,N-Di(2-hydroxyethyl)glycine | | | | | | |
| Other masking agent | Sodium silicate pentahydrate | | 10.0 | 10.0 | | | |
| | Phosphoric acid | | | | 10.0 | | |
| | Aluminum nitrate | | | | | 10.0 | 30.0 |
| Preservation stability of coloring liquid | 40° C., 60 days | — | Poor | Poor | Good | Good | Good |
| | 50° C., 60 days | — | Poor | Poor | Good | Good | Good |
| | 60° C., 60 days | — | Poor | Poor | Good | Good | Good |
| Firing temperature (° C.)[*1] | | 1550 | 1550 | 1550 | 1550 | 1550 | 1550 |
| Shade after firing | $L^*$ | 86.48 | 92.60 | 84.61 | 93.51 | 87.52 | 86.11 |
| | $a^*$ | −2.89 | −1.81 | −1.59 | −1.80 | −2.91 | -2.95 |
| | $b^*$ | 3.81 | 3.58 | 9.31 | 3.78 | 4.11 | 4.55 |
| | Chroma $C^*$ | 4.78 | 4.01 | 9.45 | 4.19 | 5.04 | 5.42 |
| Transparency ΔL* of zirconia sintered body | | 16.18 | 4.66 | 1.27 | 2.48 | 13.55 | 12.44 |
| Percentage change of transparency (%) | | — | −71.2 | −92.2 | −84.7 | −16.3 | −23.1 |
| Visual degree of masking with zirconia sintered body | | Poor | Good | Good | Good | Poor | Poor |
| Visual shade of zirconia sintered body | | White | White | Pale yellow | White | White | White |
| Biaxial flexural strength of zirconia sintered body (MPa) | | 647 | 637 | 635 | 580 | 668 | 609 |
| Percentage change of biaxial flexural strength (%) | | — | −1.5 | −1.9 | −10.4 | 3.2 | −5.9 |

[*1] In the Table, "Firing temperature" means the highest temperature in firing. Conditions other than firing temperature: Temperature increase from room temperature to 1,550° C. at 10° C./min; retention at 1,550° C. for 2 hours; temperature decrease at −10° C./min and left to cool from 300° C. to room temperature.

TABLE 3

| Components (mass %) | | Ex. 2-1 | Ex. 2-2 | Ex. 2-3 | Ex. 2-4 | Ex. 2-5 | Ex. 2-6 | Ex. 2-7 |
|---|---|---|---|---|---|---|---|---|
| Alkylsilane Compound | KBM-403 | 4.00 | 10.0 | 20.0 | 50.0 | 0.500 | 4.00 | 10.0 |
| | KBM-602 | | | | | | | |
| | KBM-903 | | | | | | | |
| | Trimethylsilanol | | | | | | | |
| Coloring component | Chromium(III) acetate | | | | | 0.300 | 0.300 | 0.400 |
| | Vanadyl(IV) oxalate | | | | | 0.300 | 0.300 | 0.400 |
| Solvent | Purified water | 96.0 | 90.0 | 80.0 | 50.0 | 98.9 | 95.4 | 89.2 |
| | Ethanol | | | | | | | |
| | Propylene glycol | | | | | | | |
| | Acetone | | | | | | | |
| Thickener | Xanthan gum | | | | | | | |
| Complexing agent | N,N-Di(2-hydroxyethyl)glycine | | | | | | | |
| Other masking agent | Sodium silicate pentahydrate | | | | | | | |
| | Phosphoric acid | | | | | | | |
| | Aluminum nitrate | | | | | | | |

TABLE 3-continued

| | | | | | | | | |
|---|---|---|---|---|---|---|---|---|
| Preservation stability of coloring liquid | 40° C., 60 days | Good | Good | Good | Good | Good | Good | Good |
| | 50° C., 60 days | Good | Good | Good | Good | Good | Good | Good |
| | 60° C., 60 days | Good | Good | Good | Good | Good | Good | Good |
| Firing temperature (° C.)[*1] | | 1550 | 1550 | 1550 | 1550 | 1550 | 1550 | 1550 |
| Shade after firing | L* | 92.21 | 92.49 | 92.62 | 94.57 | 85.48 | 84.18 | 82.59 |
| | a* | −2.08 | −2.10 | −2.05 | −2.06 | −1.89 | −1.96 | −2.35 |
| | b* | 4.19 | 4.21 | 4.24 | 3.95 | 15.11 | 15.61 | 18.30 |
| | Chroma C* | 4.68 | 4.71 | 4.71 | 4.45 | 15.23 | 15.73 | 18.45 |
| Transparency ΔL* of zirconia sintered body | | 8.08 | 7.00 | 6.47 | 1.30 | 9.98 | 4.29 | 3.64 |
| Percentage change of transparency (%) | | −50.1 | −56.7 | −60.0 | −92.0 | −38.3 | −73.5 | −77.5 |
| Visual degree of masking with zirconia sintered body | | Good | Good | Good | Good | Moderate | Good | Good |
| Visual shade of zirconia sintered body | | White | White | White | White | Pale yellow | Pale yellow | Pale yellow |
| Biaxial flexural strength of zirconia sintered body (MPa) | | 705 | 788 | 715 | 709 | 690 | 721 | 711 |
| Percentage change of biaxial flexural strength (%) | | 9.0 | 21.8 | 10.5 | 9.6 | 6.6 | 11.4 | 9.9 |

| Components (mass %) | | Ex. 2-8 | Ex. 2-9 | Ex. 2-10 | Ex. 2-11 | Ex. 2-12 |
|---|---|---|---|---|---|---|
| Alkylsilane Compound | KBM-403 | 50.0 | | | | |
| | KBM-602 | | 10.0 | 10.0 | | |
| | KBM-903 | | | | 10.0 | 10.0 |
| | Trimethylsilanol | | | | | |
| Coloring component | Chromium(III) acetate | 0.100 | | 0.400 | | 0.400 |
| | Vanadyl(IV) oxalate | 0.100 | | 0.400 | | 0.400 |
| Solvent | Purified water | 49.8 | 90.0 | 89.2 | 90.0 | 89.2 |
| | Ethanol | | | | | |
| | Propylene glycol | | | | | |
| | Acetone | | | | | |
| Thickener | Xanthan gum | | | | | |
| Complexing agent | N,N-Di(2-hydroxyethyl)glycine | | | | | |
| Other masking agent | Sodium silicate pentahydrate | | | | | |
| | Phosphoric acid | | | | | |
| | Aluminum nitrate | | | | | |
| Preservation stability of coloring liquid | 40° C., 60 days | Good | Good | Good | Good | Good |
| | 50° C., 60 days | Good | Good | Good | Good | Good |
| | 60° C., 60 days | Good | Good | Good | Good | Good |
| Firing temperature (° C.)[*1] | | 1550 | 1550 | 1550 | 1550 | 1550 |
| Shade after firing | L* | 90.80 | 92.21 | 82.41 | 92.05 | 82.39 |
| | a* | −3.65 | −2.56 | −2.48 | −2.43 | −2.51 |
| | b* | 11.09 | 4.45 | 18.51 | 4.61 | 18.57 |
| | Chroma C* | 11.68 | 5.13 | 18.68 | 5.21 | 18.74 |
| Transparency ΔL* of zirconia sintered body | | 0.44 | 6.88 | 3.51 | 6.59 | 3.48 |
| Percentage change of transparency (%) | | −97.3 | −57.5 | −78.3 | −59.3 | −78.5 |
| Visual degree of masking with zirconia sintered body | | Good | Good | Good | Good | Good |
| Visual shade of zirconia sintered body | | Pale yellow | White | Pale yellow | White | Pale yellow |
| Biaxial flexural strength of zirconia sintered body (MPa) | | 715 | 691 | 689 | 682 | 699 |
| Percentage change of biaxial flexural strength (%) | | 10.5 | 6.8 | 6.5 | 5.4 | 8.0 |

[*1]In the Table, "Firing temperature" means the highest temperature in firing. Conditions other than firing temperature: Temperature increase from room temperature to 1,550° C. at 10° C./min; retention at 1,550° C. for 2 hours; temperature decrease at −10° C./min and left to cool from 300° C. to room temperature.

TABLE 4

| Components (mass %) | | Ex. 2-13 | Ex. 2-14 | Ex. 2-15 | Ex. 2-16 | Ex. 2-17 | Ex. 2-18 |
|---|---|---|---|---|---|---|---|
| Alkylsilane Compound | KBM-403 | | 10.0 | 10.0 | 10.0 | 10.0 | 10.0 |
| | KBM-602 | | | | | | |
| | KBM-903 | | | | | | |
| | Trimethylsilanol | 3.00 | | | | | |
| Coloring component | Chromium(III) acetate | 0.300 | 0.400 | 0.400 | 0.400 | 0.400 | 0.400 |
| | Vanadyl(IV) oxalate | 0.300 | 0.400 | 0.400 | 0.400 | 0.400 | 0.400 |
| Solvent | Purified water | 96.4 | 10.0 | 10.0 | 10.0 | 88.9 | 89.1 |
| | Ethanol | | 79.2 | | | | |
| | Propylene glycol | | | 79.2 | | | |
| | Acetone | | | | 79.2 | | |
| Thickener | Xanthan gum | | | | | 0.300 | |
| Complexing agent | N,N-Di(2-hydroxyethyl)glycine | | | | | | 0.100 |
| Other masking agent | Sodium silicate pentahydrate | | | | | | |
| | Phosphoric acid | | | | | | |
| | Aluminum nitrate | | | | | | |

TABLE 4-continued

| Components (mass %) | | Ex. 2-13 | Ex. 2-14 | Ex. 2-15 | Ex. 2-16 | Ex. 2-17 | Ex. 2-18 |
|---|---|---|---|---|---|---|---|
| Preservation stability of coloring liquid | 40° C., 60 days | Good | Good | Good | Good | Good | Good |
| | 50° C., 60 days | Good | Good | Good | Good | Good | Good |
| | 60° C., 60 days | Good | Good | Good | Good | Good | Good |
| Firing temperature (° C.)*1 | | 1550 | 1550 | 1550 | 1550 | 1550 | 1550 |
| Shade after firing | L* | 84.55 | 82.68 | 82.34 | 82.51 | 82.71 | 82.43 |
| | a* | −1.91 | −2.45 | −2.3 | −2.37 | −2.47 | −2.38 |
| | b* | 15.32 | 18.90 | 18.21 | 18.41 | 18.91 | 18.51 |
| | Chroma C* | 15.44 | 19.06 | 18.36 | 18.56 | 19.07 | 18.66 |
| Transparency ΔL* of zirconia sintered body | | 8.01 | 3.61 | 3.71 | 3.65 | 3.59 | 3.55 |
| Percentage change of transparency (%) | | −50.5 | −77.7 | −77.1 | −77.4 | −77.8 | −78.1 |
| Visual degree of masking with zirconia sintered body | | Good | Good | Good | Good | Good | Good |
| Visual shade of zirconia sintered body | | Pale yellow | Pale yellow | Pale yellow | Pale yellow | Pale yellow | Pale yellow |
| Biaxial flexural strength of zirconia sintered body (MPa) | | 672 | 708 | 712 | 703 | 721 | 717 |
| Percentage change of biaxial flexural strength (%) | | 3.9 | 9.4 | 10.0 | 8.7 | 11.4 | 10.8 |

*1In the Table, "Firing temperature" means the highest temperature in firing. Conditions other than firing temperature: Temperature increase from room temperature to 1,550° C. at 10° C./min; retention at 1,550° C. for 2 hours; temperature decrease at −10° C./min and left to cool from 300° C. to room temperature.

The preservation stability was poor, and gelation was visually confirmed during storage in Comparative Examples 1-2 and 1-3 in which inorganic silicon compounds were contained. A decrease of biaxial flexural strength was confirmed in the zirconia sintered body of Comparative Example 1-4 in which phosphoric acid was added. The color of the metallic abutment tooth was visible through the sintered body, and the masking properties were insufficient in Comparative Examples 1-5 and 1-6 in which water-soluble aluminum was added.

In contrast, there was no decrease in the strength of the zirconia sintered body, and good preservation stability and superior masking properties were confirmed in Examples 1-1 to 1-24, and 2-1 to 2-18 in which organosilicon compounds were contained. The preservation stability was desirable and the masking properties were superior, and it was possible to impart the desired color in Examples 1-5 to 1-7, 1-10, 1-11, 1-17 to 1-24, 2-5 to 2-8, 2-10, and 2-12 to 2-18 in which coloring components were contained.

INDUSTRIAL APPLICABILITY

A dental ceramic coloring liquid of the present invention can reduce a decrease in the mechanical strength of a dental ceramic after sintering, and can impart masking properties while having good preservation stability. A dental ceramic coloring liquid of the present invention, when containing a coloring component, can impart the desired shade to a dental ceramic while imparting masking properties. This enables a dental ceramic coloring liquid of the present invention to be suitably used as a coloring liquid for coloring a dental ceramic. A dental ceramic coloring liquid of the present invention with masking properties is useful given an expected increase in the use of dental ceramic coloring liquids, particularly in response to the continuously growing demand for ceramic dental caps and the associated increase in individual demand for better aesthetics.

The invention claimed is:

1. A coloring liquid for coloring a dental ceramic, comprising:

(i) an organosilicon compound;

(ii) a coloring component; and (iii) water and/or an organic solvent, wherein:

the organosilicon compound is an alkylsilane compound, the coloring component comprises at least one component selected from the group consisting of Al, K, Zr, Cr, Na, V, Y, Gd, La, Yb, Tm, Ni, Mn, Co, Nd, Pr, Tb, and Er, and the coloring component does not comprise Cu, if present, the organic solvent consists of one or more solvents selected from the group consisting of an alcohol, a glycol, a triol, and a ketone, and the coloring liquid does not comprise a phosphorus-containing component.

2. The coloring liquid according to claim 1, wherein the organosilicon compound is hydrophilic.

3. The coloring liquid according to claim 1, wherein the alkylsilane compound is a compound represented by the following general formula (2),

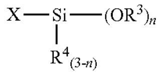

(2)

wherein $R^3$ represents an optionally substituted linear or branched alkyl group, $R^4$ represents an optionally substituted linear or branched alkyl group, an optionally substituted aryl group, or a halogen atom, n is an integer of 0 to 3, and X represents —$R^5$—$Y^1$, —$Y^1$, —$R^5$—$B^1$-$A^1$, —$R^5$-$A^1$, or -$A^1$, where $R^5$ is an optionally substituted linear or branched alkylene group or a cycloalkylene group, and the alkylene group or the cycloalkylene group may contain a —$CH_2$—$C_6H_4$— ($C_6H_4$ represents a phenylene group), —S—, —NH—, —$NR^6$—, —C(O)—O—, or —O— group, where $R^6$ represents an optionally substituted linear or branched alkyl group, an optionally substituted cycloalkyl group, or an optionally substituted aryl group, $Y^1$ represents a hydroxyl group, an optionally substituted alkoxy group, an optionally substituted amino group, a mercapto group, an epoxy group, a halogen atom, or an optionally substituted amine salt, $B^1$ represents —C(O)—O—, —C(O)—S—, —C(O)—NH—, —NH—C(O)—NH—, —NH—C(O)—S—, or —NH—C(O)—O—, and $A^1$ represents $H_2C{=}CH$—, $H_2C{=}C(CH_3)$—, or $H_2C{=}CH$—$C_6H_4$— ($C_6H_4$ represents a phenylene group).

4. The coloring liquid according to claim 3, wherein, in compounds represented by the general formula (2), X represents —$R^5$—$Y^1$ or —$Y^1$, and $Y^1$ is a hydroxyl group, an optionally substituted amino group, an epoxy group, or an optionally substituted amine salt.

5. The coloring liquid according to claim 4, wherein X represents —$R^5$—$Y^1$, $R^5$ , is an optionally substituted linear or branched alkylene group, and the alkylene group may contain a —$CH_2$—$C_6H_4$—($C_6H_4$ represents a phenylene group), —S—, —NH—, —$NR^6$—, —C(O)—O—, or —O- group.

6. The coloring liquid according to claim 1, wherein the alkylsilane compound is at least one compound selected from the group consisting of trimethylsilanol, 2-(3,4-epoxycyclohexyl)ethyltrimethoxysilane, 3-glycidoxypropylmethyldimethoxysilane, 3-glycidoxypropyltrimethoxysilane, 3-glycidoxypropylmethyldiethoxysilane, 3-glycidoxypropyltriethoxysilane, N-2-(aminoethyl)-3-aminopropylmethyldimethoxysilane, N-2-(aminoethyl)-3-aminopropyltrimethoxysilane, 3-phenylaminopropyltrimethoxysilane, 3-aminopropyltrimethoxysilane, and 3-aminopropyltriethoxysilane.

7. The coloring liquid according to claim 1, wherein the content of the alkylsilane compound is 0.1 to 60 mass %.

8. The coloring liquid according to claim 1, wherein the coloring component is an ion or a complex.

9. The coloring liquid according to claim 1, wherein the dental ceramic comprises zirconia as a main component.

10. The coloring liquid according to claim 1, comprising the water.

11. The coloring liquid according to claim 1, comprising the organic solvent.

12. The coloring liquid according to claim 1, comprising the water and the organic solvent.

* * * * *